United States Patent
Eibl

(10) Patent No.: US 10,251,838 B2
(45) Date of Patent: Apr. 9, 2019

(54) STEREOSPECIFIC LIPIDS FOR LOCOREGIONAL THERAPY WITH LONG-TERM CIRCULATING STIMULI-SENSITIVE NANOCARRIER SYSTEMS

(71) Applicant: THERMOSOME GmbH, Planegg/Martinsried (DE)

(72) Inventor: Hansjörg Eibl, Bovenden (DE)

(73) Assignee: THERMOSOME GMBH, Planegg/Martinsried (DE)

( * ) Notice: Subject to any disclaimer, the term of this patent is extended or adjusted under 35 U.S.C. 154(b) by 0 days.

(21) Appl. No.: 14/899,174

(22) PCT Filed: Jun. 18, 2014

(86) PCT No.: PCT/EP2014/062849
§ 371 (c)(1),
(2) Date: Dec. 17, 2015

(87) PCT Pub. No.: WO2014/202680
PCT Pub. Date: Dec. 24, 2014

(65) Prior Publication Data
US 2016/0136092 A1    May 19, 2016

(30) Foreign Application Priority Data

Jun. 18, 2013  (EP) ..................... 13172469

(51) Int. Cl.
| A61K 9/127  | (2006.01) |
| A61K 31/56  | (2006.01) |
| A61K 31/575 | (2006.01) |
| A61K 31/683 | (2006.01) |
| A61K 31/685 | (2006.01) |
| A61K 31/704 | (2006.01) |
| C07F 9/02   | (2006.01) |
| A61K 9/00   | (2006.01) |
| C07F 9/10   | (2006.01) |
| A61K 45/06  | (2006.01) |
| A61K 47/24  | (2006.01) |

(52) U.S. Cl.
CPC ............ *A61K 9/127* (2013.01); *A61K 9/0019* (2013.01); *A61K 31/704* (2013.01); *A61K 45/06* (2013.01); *A61K 47/24* (2013.01); *C07F 9/10* (2013.01); *C07F 9/106* (2013.01)

(58) Field of Classification Search
CPC .... A61K 9/127; A61K 31/704; A61K 31/685; A61K 31/575; A61K 31/56; C07F 9/10
See application file for complete search history.

(56) References Cited

U.S. PATENT DOCUMENTS

| 6,413,543    | B1  | 7/2002  | Eibl          |            |
|--------------|-----|---------|---------------|------------|
| 2004/0137048 | A1  | 7/2004  | Eibl et al.   |            |
| 2004/0213836 | A1* | 10/2004 | Eibl          | A61K 9/1271 |
|              |     |         |               | 424/450    |
| 2005/0042774 | A1* | 2/2005  | McIntyre      | G01N 33/54306 |
|              |     |         |               | 436/530    |
| 2006/0165767 | A1  | 7/2006  | Eibl et al.   |            |
| 2009/0214634 | A1* | 8/2009  | Chaber        | A61K 9/08  |
|              |     |         |               | 424/450    |
| 2010/0260683 | A1* | 10/2010 | Eibl          | A61K 9/127 |
|              |     |         |               | 424/9.6    |

FOREIGN PATENT DOCUMENTS

| EP | 0319136    | A1 * | 6/1989  | ............ A61K 9/127  |
| EP | 2638896    | A1 * | 9/2013  | ........... A61K 9/1272 |
| JP | 2000506121 |      | 5/2000  |                          |
| JP | 2002518317 |      | 6/2002  |                          |
| JP | 2009269846 |      | 11/2009 |                          |
| WO | 9730058    |      | 8/1997  |                          |
| WO | 9965466    |      | 12/1999 |                          |
| WO | 02064116   |      | 8/2002  |                          |
| WO | 2004026282 |      | 4/2004  |                          |

OTHER PUBLICATIONS

Derycke et al., "Transferrin-Conjugated Liposome Targeting of Photosensitizer AlPcS4 to Rat Bladder Carcinoma Cells", Journal of the National Cancer Institute 96.21 (2004).

Hossann et al., "In vitro stability and content release properties of phosphatidylglyceroglycerol containing thermosensitive liposomes", Biochimica et Biophysica Acta (BBA)—Biomembranes 1768.10 (2007): 2491-2499.

Landon et al., "Nanoscale Drug Delivery and Hyperthermia: The Materials Design and Preclinical and Clinical Testing of Low Temperature-Sensitive Liposomes Used in Combination with Mild Hyperthermia in the Treatment of Local Cancer", The Open Nanomedicine Journal, 2011, 3, 38-64.

PCT/EP2014/062849, International Application No. PCT/EP2014/062849, "International Search Report" with English translation, dated Oct. 1, 2014.

Bassett et al., Use of Temperature-Sensitive Liposomes in the Selective Delivery of Methotrexate and Cis-Platinum Analogues to Murine Bladder Tumor, The Journal of Urology, vol. 135, No. 3, Mar. 1986, pp. 612-615.

Lindner et al., Novel Temperature-Sensitive Liposomes with Prolonged Circulation Time, Clinical Cancer Research, vol. 10, No. 6, Mar. 15, 2004, pp. 2168-2178.

Ali et al., "Synthesis of short and long chain cardiolipins", Tetrahedron 62 (2006): 6990-6997.

Benson et al., "Plant phospholipids I. Identification of the phosphatidyl glycerols", Biochimica et biophysica acta 27 (1958): 189-195.

(Continued)

*Primary Examiner* — Tracy Liu

(74) *Attorney, Agent, or Firm* — Kilpatrick Townsend & Stockton LLP

(57) ABSTRACT

The invention relates to stereospecific lipids for the locoregional therapy with long-term circulating stimuli-sensitive nanocarrier systems. A preferred embodiment thereof is a thermosensitive liposome for treating tumors, especially urinary bladder tumors and other localized tumors.

38 Claims, 6 Drawing Sheets

(56) References Cited

OTHER PUBLICATIONS

Figure 1:
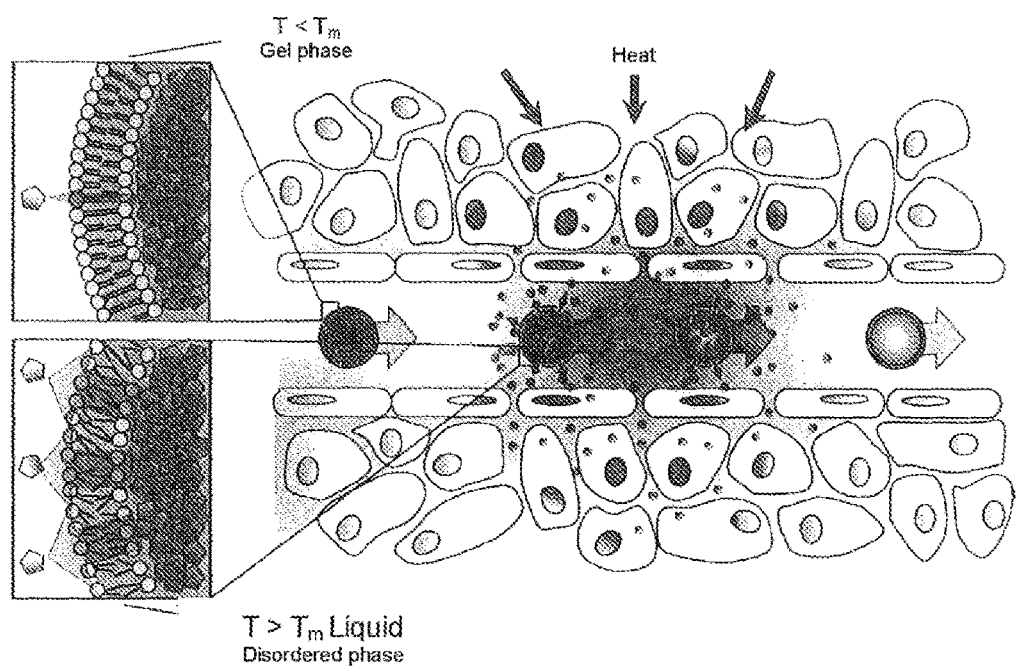

Benson et al., "The phosphatidylglycerol and sulpholipid of plants. Asymmetry of the glycerol moiety", Proceedings of the Biochemical Society, 81, 31 p (1961).
Chang et al., "Biosynthesis of phosphatidyl glycerophosphate in *Escherichia coli*", Journal of Lipid Research 8.5 (1967): 447-455.
Eibl, "Synthesis of glycerophospholipids", Chemistry and physics of lipids 26.4 (1980): 405-429.
Eibl, "An improved method for the preparation of 1, 2-isopropylidene-sn-glycerol", Chemistry and Physics of Lipids 28 (1981): 1-5.
Eibl et al., "Synthesis of enantiomerically pure glyceryl esters and ethers. I. Methods employing the precursor 1, 2-isopropylidene-sn-glycerol", Chemistry and physics of lipids 41.1 (1986): 53-63.
Eibl et al., "Synthesis of enantiomerically pure glyceryl esters and ethers. II. Methods employing the precursor 3, 4-isopropylidene-D-mannitol", Chemistry and physics of lipids 47 (1988): 47-53.
Grit et al., "Chemical stability of liposomes: implications for their physical stability", Chemistry and physics of lipids 64 (1993): 3-18.
Harlos et al., "Influence of calcium on phosphatidylglycerol. Two separate lamellar structures", Biochemistry 19 (1980): 895-899.
Haverkate et al., "Isolation and chemical characterization of phosphatidyl glycerol from spinach leaves", Biochimica et Biophysica Acta (BBA) 106 (1965): 78-92.
Haverkate et al., "The enzymic hydrolysis and structure of phosphatidyl glycerol", Biochimica et biophysica acta 63.3 (1962): 547-549.
Haverkate et al., "The stereochemical configuration of phosphatidyl glycerol", Biochimica et Biophysica Acta 84 (1964): 106-108.
IUPAC-IUB Commission on Biochemi, "The Nomenclature of Lipids", Chemistry and Physics of Lipids 21 (1978) 159-173.
Joutti et al., "The structure of phosphatidyl glycerol prepared by phospholipase D-catalyzed transphosphatidylation from egg lecithin and glycerol", Chemistry and physics of lipids 17.2-3 (1976): 264-266.
Kiyasu et al., "The biosynthesis of phosphatidylglycerol", The Journal of Biological Chemistry 238 (1963): 2293-2298.
Op Den Kamp et al., "Structural investigations on glucosaminyl phosphatidylglycerol from *Bacillus megaterium*", Biochimica et Biophysica Acta (BBA) 176 (1969): 298-305.
Ruettinger et al., "Stereoconfiguration of phosphatidylglycerol in the membrane of bacteriophage PM2 and in its host, *Pseudomonas* BAL-31", Biochimica et Biophysica Acta (BBA) 529 (1978): 181-185.
Slotboom et al., "Recent developments in the chemistry of phospholipids", Chemistry and physics of lipids 5 (1970): 301-398.
Tocanne et al., "Chemical and physicochemical studies of lysylphosphatidylglycerol derivatives. Occurrence of A2'→ 3' lysyl migration", Chemistry and physics of lipids 13 (1974): 389-403.
Van Hoogevest et al., "The use of natural and synthetic phospholipids as pharmaceutical excipients", European journal of lipid science and technology 116.9 (2014): 1088-1107.
Yang et al., "Transphosphatidylation by phospholipase D", Journal of Biological Chemistry 242.3 (1967): 477-484.

\* cited by examiner

STEREOSPECIFIC LIPIDS FOR LOCOREGIONAL THERAPY WITH LONG-TERM CIRCULATING STIMULI-SENSITIVE NANOCARRIER SYSTEMS

PRIOR RELATED APPLICATIONS

This application is a National Phase application of International Application No. PCT/EP2014/062849, filed Jun. 18, 2014, which claims priority to European Application No. 13172469.2, filed Jun. 18, 2013, each of which is incorporated herein by reference in its entirety.

The present application relates to stereospecific lipids for locoregional therapy with long-term circulating stimuli-sensitive nanocarrier systems.

The present application relates in particular to a thermosensitive liposome for treating tumours, in particular bladder tumours and other localised tumours.

The present application relates in particular to the treatment of the bladder tumour with long-term circulating thermosensitive liposomes. The therapeutic approach is, however, of general clinical importance since it can be used generally for the therapy of diseases in humans and in animals by means of the locoregional release of medicinal drugs, and in particular also in the case of other tumour diseases which are caused by the localised settlement of tumour cells in organs and body tissue.

The application relates further to phospholipids having a uniform and natural configuration which can be used in particular as constituents of the nanocarrier systems according to the invention, for example as constituents of liposomes.

Bladder carcinoma is a frequent oncological disease. Worldwide, approximately 130,000 people die of a bladder carcinoma each year. Men suffer twice as frequently as women, the average age of onset being 69 for men and 73 for women. Approximately 95% of bladder carcinomas are of urothelial origin. Clinically, it is especially important to distinguish between a low-grade and a high-grade tumour, because there is a very high risk of recurrence and progression with the latter. Histological detection of a bladder tumour with determination of the infiltration depth is carried out by a transurethral resection of the tumour (TURB). In all high-grade and T1 tumours (that is to say with infiltration of the lamina propria), follow-up transurethral resection is necessary two to six weeks after the initial operation. If the tumour has invaded the muscle layer, radical cystectomy is indicated.

In addition to the surgical approach, intravesical chemotherapy, that is to say instillation of mitomycin C, doxorubicin or epirubicin, is a proven method of treating bladder tumours. After resection of a low-risk tumour, only early instillation (within the first 6 hours postoperatively) is recommended, whereas maintenance therapy with repeated chemotherapy instillations is additionally recommended in the case of intermediate-risk and high-risk tumours. Some instillations are carried out at weekly intervals and can be continued for several months. An alternative to the instillation of chemotherapy is the instillation of BCG (bacillus Calmette-Guerin).

Despite TURB and intravesical chemotherapy, there is a high risk of recurrence for superficial bladder carcinomas. The effectiveness of intravesical chemotherapy is limited by the restricted depth of penetration into the bladder, because the urothelium layer represents a very effective barrier for cytostatics. Seen from the inside of the bladder outwards, the bladder wall is composed of the following tissue: urothelium, lamina propria, tunica muscularis and adventitia. After instillation of cytostatics into the bladder, the tissue concentration decreases semi-logarithmically with increasing tissue depth. In humans, it has been possible to show that, from an infiltration depth of 500 µm, only 50% of the initial tissue concentration is still present (Wientjes M G et al. Penetration of mitomycin C in human bladder. Cancer Res. 1993). Using a dog model, it has been possible to show that cytotoxic concentrations for mitomycin C can be achieved only within the urothelium layer, whereas sufficiently high concentrations were achieved in the lamina propria in only 20% of cases and in the tunica muscularis in less than 20% of cases. For example, in this study, a median concentration of mitomycin C of 1 µg/g (n=24) was detectable at a tissue depth of 2000 µm. At a tissue depth of 2000-3000 µm, no further mitomycin C was detectable in 18/24 dogs (Wientjes M G et al. Bladder wall penetration of intravesical mitomycin C in dogs. Cancer Res. 1991). In summary, the effectiveness of intravesical chemotherapy is limited very greatly by inadequate penetration of the cytostatics that are used.

Accordingly, it was an object of the invention to provide a treatment option for treating localised diseases, and preferably tumours, and in particular bladder tumours and other localised tumours.

The object is achieved according to the invention by a stimuli-sensitive nanocarrier system for use in locoregional therapy.

The nanocarrier system according to the invention is preferably liposomes. However, other nanocarrier systems can also be used. It is essential to the invention that the nanocarrier systems, in particular liposomes, are stimuli-sensitive. The stimuli-sensitive nanocarrier systems, in particular stimuli-sensitive liposomes, according to the invention release an enclosed or associated active ingredient in response to the exertion of a stimulus. Suitable stimuli or energy sources are preferably heat, radio frequency, for example radiative superficial and deep hyperthermia systems or bladder hyperthermia systems, ultrasound, such as highly focused ultrasound (HIFU) or low-intensity ultrasound (LIFU), light, laser, conduction through heated fluid, or other physical principles which lead to locoregional heating and/or destabilise membranes, in particular membranes comprising phospholipids.

By means of locoregional therapy, in particular by the targeted and rapid release of active ingredients enclosed in the stimuli-sensitive nanocarrier systems, localised diseases can be treated in a targeted manner without damaging healthy tissue. In addition, the systemic load is kept to a minimum by the targeted release of active ingredients.

The invention relates in particular to a stimuli-sensitive, preferably thermosensitive, liposome for use in the treatment of tumours and in particular of bladder tumours. By using thermosensitive liposomes, an active ingredient enclosed in the liposomes can be released by targeted heating of the liposomes. Such thermosensitive liposomes are therefore particularly suitable for the local therapy of tumours and in particular of bladder tumours, or bladder carcinomas. The release of the active ingredient enclosed in the liposomes can be induced at the desired site in the body, for example in the bladder wall, in a targeted manner whereby the active ingredient, in particular a cytostatic, can be released directly at the desired site.

The stimuli-sensitive nanocarrier system, in particular a thermosensitive liposome, used according to the invention particularly preferably comprises (i) at least one phosphatidylcholine having a main transition temperature of from 0°

C. to 80° C. and (ii) at least one phosphatidyloligoglycerol and/or phosphatidylglyceroglycol and/or at least one cardiolipin.

By using phosphatidyloligoglycerols, it has been possible to prepare thermosensitive liposomes having a prolonged blood circulation time (WO 2002/064116 and WO 2004/026282). These liposomes are very stable in the bloodstream under physiological conditions (37-38° C.), for example, and do not release, or release only insubstantially, an active ingredient previously enclosed in the liposome (Lindner L H et al. Novel temperature-sensitive liposomes with prolonged circulation time. Clin Cancer Res. 2004; Hossann M et al. In vitro stability and content release properties of phosphatidylglyceroglycerol containing thermosensitive liposomes. Biochim Biophys Acta. 2007). The majority of the liposomes remain in the blood circulation over a period of 2 hours and are therefore available for heat-controlled release of the active ingredient. Owing to the rapid release-kinetics of these liposomes with heat-induced release of the active ingredient within a few seconds, preferably <15 seconds, more preferably <10 seconds, a previously enclosed active ingredient can be released immediately by targeted heating of the liposomes to temperatures >39° C., preferably 40-42° C.

As a result of the high stability of the liposomes according to the invention in the systemic circulation with only very low non-specific release of the active ingredient, these liposomes are suitable in a very specific manner for the local therapy of tumours, in particular of localised tumours and particularly preferably of bladder carcinoma. After intravenous administration of the liposomes according to the invention, the release of a previously enclosed active ingredient at the desired site, for example in the bladder wall, can be induced by targeted heating of the desired site, for example the bladder wall.

By means of this method, the natural barrier of the urothelium can be overcome and, for the first time, high tissue levels of the enclosed medicinal drug can be achieved as far as the tunica muscularis.

According to the invention, tumours, in particular solid and/or localised tumours, are treated. Superficial tumours and metastases in particular can be treated with the liposomes according to the invention because they can be heated in a simple manner. However, other tumours, for example tumours in hollow organs, can also be treated. In this case, the heating required to release the contents of the liposomes can be achieved for example by flushing with warm water. Examples thereof are ENT tumours, lymph node tumours, lung tumours, peritoneal carcinomas, pleural carcinomas, oesophageal carcinomas, stomach carcinomas and bladder carcinomas.

A bladder tumour, or bladder carcinoma, is most preferably treated according to the invention. It is possible to treat both the carcinoma in situ and stage T1 as well as other stages, for example T2 or T3, of the bladder carcinoma.

In addition to the therapy of superficial bladder tumours, such a method can also be used for the therapy of muscle-invasive tumours in order to ensure that the bladder is preserved. The advantage that is achieved by this method as compared with the administration of intravesical chemotherapy in terms of improved tumour control and an increased rate of bladder-preserving treatments associated with a low rate of systemic side effects suggests that this method will replace conventional intravesical chemotherapy instillation.

The liposomes according to the invention preferably further comprise an active ingredient, in particular a cytostatic. In addition to the cytostatics mitomycin C, doxorubicin and epirubicin which are conventionally used for intravesical therapy, other cytostatics such as gemcitabine, trabectedin, etc. can also be used for this approach. Further suitable cytostatics are platinum derivatives such as cisplatin, carboplatin or oxaliplatin. Doxorubicin is most preferable as the active ingredient.

The organ in question, for example the bladder, can be heated technically using a wide variety of methods. For example, in addition to simple flushing of the bladder with warm water, heating can also be carried out by electromagnetic waves, ultrasound or by laser techniques.

Stimuli-sensitive nanocarrier systems, in particular thermosensitive liposomes, which comprise at least (i) a phosphatidylcholine having a main transition temperature of from 0° C. to 80° C. and (ii) at least one phosphatidyloligoglycerol and/or phosphatidylglyceroglycol and/or cardiolipin have a long half-life in serum. In addition, the contents of such nanocarrier systems, in particular liposomes, are released rapidly, in particular in less than 10 seconds, under the exertion of a stimulus, for example when a particular temperature is exceeded.

A constituent of stimuli-sensitive nanocarrier systems, in particular thermosensitive liposomes, that are preferable according to the invention is a phosphatidylcholine. The phosphatidylcholine is present preferably in an amount of at least 1 wt. %, more preferably of at least 10 wt. %, yet more preferably of at least 30 wt. % and even more preferably of at least 50 wt. %, and up to 99 wt. %, more preferably up to 90 wt. % and particularly preferably up to 80 wt. %, based on the total weight of the stimuli-sensitive nanocarrier systems, in particular liposomes.

By selecting a phosphatidylcholine having a suitable main transition temperature, the stimuli-sensitive nanocarrier system, in particular the thermosensitive liposome, can be customised. Table 1 gives main transition temperatures ($T_M$) of phosphatidylcholines whose main transition temperatures are in the range of from 0 to 80° C. As can be seen from the table, the main transition temperatures are dependent on the chain length and on the distribution over positions 1 and 2 of glycero-3-phosphocholine or over positions 1 and 3 of glycero-2-phosphocholine.

TABLE 1

Phase transition temperatures ($T_M$) of phospholipids

| $T_M$ | phosphatidylcholine/phosphatidyldiglycerol/ phosphatidyltriglycerol/phosphatidyltetraglycerol |
|---|---|
| 5° C. | 1-palmitoyl-2-oleoyl- |
| 7° C. | 1-stearoyl-2-oleoyl- |
| 11° C. | 1-palmitoyl-2-lauroyl- |
| 14° C. | 1-behenoyl-2-oleoyl- |
| 17° C. | 1-stearoyl-2-lauroyl- |
| 19° C. | 1,3-dimyristoyl- |
| 23° C. | 1,2-dimyristoyl- |
| 27° C. | 1-palmitoyl-2-myristoyl- |
| 33° C. | 1-stearoyl-2-myristoyl- |
| 37° C. | 1-myristoyl-2-palmitoyl- |
| 39° C. | 1,3-dipalmitoyl- |
| 41° C. | 1,2-dipalmitoyl- |
| 42° C. | 1-myristoyl-2-stearoyl- |
| 46° C. | 1-stearoyl-3-myristoyl- |
| 48° C. | 1-stearoyl-2-palmitoyl- |
| 52° C. | 1-palmitoyl-2-stearoyl- |
| 53° C. | 1,3-distearoyl- |
| 56° C. | 1,2-distearoyl- |
| 66° C. | 1,2-diarachinoyl- |
| 75° C. | 1,2-dibehenoyl- |
| 80° C. | 1,2-dilignoceroyl- |

The values listed in Table 1 show that, by using the indicated fatty acids having uneven chain length and suitable distribution over the glycerol basic structure, virtually any desired temperature in the indicated range of from 0 to 80° C. can be set. The fatty acid chains and their distribution over positions 1 and 2 of the glycerol molecule dominate the physical properties of the phospholipids. The phase transition temperature is independent of whether the phospholipid is the phosphatidylcholine, the phosphatidyldiglycerol, the phosphatidyltriglycerol or the phosphatidyltetraglycerol.

The stimuli-sensitive nanocarrier system, in particular the thermosensitive liposome, according to the invention preferably comprises a phosphatidylcholine of formula (I)

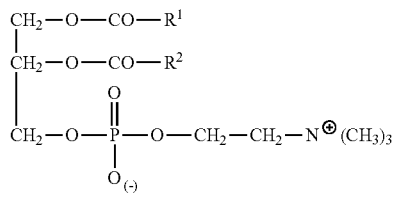

wherein $R^1$ and $R^2$ each independently represent a hydrocarbon functional group having from 12 to 24 carbon atoms.

$R^1$ and $R^2$ are preferably each independently of the other a saturated or mono- or poly-unsaturated, preferably linear alkyl functional group, in particular a saturated alkyl functional group, $R^1$ and $R^2$ are further preferably each independently a C14 to C20, in particular a C14 to C18 functional group.

Preferably, $R^1$ and $R^2$ are each independently a linear saturated C12- to C24-, in particular C12- to C20-alkyl functional group.

Most preferably, $R^1$ and $R^2$ are independently a linear saturated C14-, C16- or C18-alkyl functional group.

In a further embodiment, $R^1$ and $R^2$ are preferably each independently a C13 to C19, in particular a C13 to C17 functional group. Most preferably, $R^1$ and $R^2$ are independently a linear saturated C13-, C15- or C17-alkyl functional group.

Suitable phosphatidylcholines are, for example, 1-palmitoyl-2-oleoylglycero-3-phosphocholine, 1-stearoyl-2-oleoyl-3-phosphocholine, 1-palmitoyl-2-lauroylglycero-3-phosphocholine, 1-behenoyl-2-oleoylglycero-3-phosphocholine, 1-stearoyl-2-lauroylglycero-3-phosphocholine, 1,3-dimyristoylglycero-2-phosphocholine, 1,2-dimyristoylglycero-3-phosphocholine, 1-palmitoyl-2-myristoylglycero-3-phosphocholine, 1-stearoyl-2-myristoylglycero-3-phosphocholine, 1-myristoyl-2-palmitoylglycero-3-phosphocholine, 1,3-palmitoylglycero-2-phosphocholine, 1,2-dipalmitoylglycero-3-phosphocholine, 1-myristoyl-2-stearoylglycero-3-phosphocholine, 1-stearoyl-3-myristoylglycero-2-phosphocholine, 1-stearoyl-2-palmitoylglycero-3-phosphocholine, 1-palmitoyl-2-stearoylglycero-3-phosphocholine, 1,3-distearoylglycero-2-phosphocholine, 1,2-distearoylglycero-3-phosphocholine, 1,2-diarachinoylglycero-3-phosphocholine, 1,2-dibehenoylglycero-3-phosphocholine and 1,2-dilignoceroylglycero-3-phosphocholine.

The stimuli-sensitive nanocarrier system, in particular thermosensitive liposome, particularly preferably comprises at least one phosphatidylcholine having a main transition temperature in the range of from 35° C. to 42° C., yet more preferably in the range of from 39° C. to 41° C. Stimuli-sensitive nanocarrier systems, in particular thermosensitive liposomes, which comprise such phosphatidylcholines have a release temperature for the contents which allows the liposomes to be stable in normal circulation (at 37° C.) and to release their contents owing to the action of heat, in particular the local action of heat, at temperatures above 39° C. to 41° C. Stimuli-sensitive nanocarrier systems, in particular thermosensitive liposomes, having a release temperature of from 40 to 43° C. are particularly preferable. The stimuli-sensitive nanocarrier systems, in particular thermosensitive liposomes, according to the invention particularly preferably comprise at least one phosphatidylcholine selected from 1,3-dipalmitoyl-phosphatidylcholine and 1,2-dipalmitoyl-phosphatidylcholine.

The stimuli-sensitive nanocarrier system, in particular thermosensitive liposome, preferably comprises a phosphatidylcholine of formula (I) in the natural configuration:

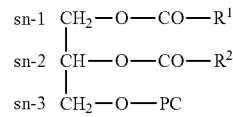

wherein
$R^1$, $R^2$ is as defined above,
sn=stereospecific numbering
PC=phosphocholine
$T_M$=phase transition temperature
Configuration: natural
Name: 1,2-diacyl-sn-glycero-3-phosphocholine Preferable phosphatidylcholines for therapeutic use are those which have a phase transition temperature around 40° C. The $T_M$ of the stimuli-sensitive nanocarrier system, in particular of the liposome, can be adjusted to the desired temperature by adding phosphatidylcholines having $T_M<40°$ C. or by adding phosphatidylcholines having $T_M>40°$ C. It has been shown that differences in the alkyl chain length of >4 $CH_2$ groups lead to phase separations and should therefore be avoided.

For other applications which are not dependent on stability at about 37° C. and active-ingredient release at 42° C., phospholipids that have a different $T_M$ of <37° C. or >45° C. CaO be used.

The stimuli-sensitive nanocarrier systems, in particular thermosensitive liposomes, according to the invention comprise as a further essential constituent at least one phosphatidyloligoglycerol and/or phosphatidylglyceroglycol and/or cardiolipin. Phosphatidyloligoglycerols comprise oligoglycerol units, in particular units of formula (III)

wherein n represents an integer from 2 to 50, in particular an integer from 2 to 10 and most preferably 2 or 3.

Preferable phosphatidyloligoglycerols have the formula (II):

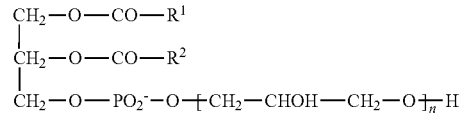

wherein $R^1$ and $R^2$ each independently represent a hydrocarbon functional group having from 12 to 24 carbon atoms and n is an integer from 2 to 50.

$R^1$ and $R^2$ are preferably each independently of the other a preferably linear saturated or mono- or poly-unsaturated alkyl functional group, in particular a saturated alkyl functional group. $R^1$ and $R^2$ are further preferably each independently a C14 to C20, in particular a C14 to C18 functional group.

Preferably, $R^1$ and $R^2$ are each independently a linear saturated C12- to C24-, in particular C12- to C20-alkyl functional group.

Most preferably, $R^1$ and $R^2$ are independently a linear saturated C14-, C16- or C18-alkyl functional group.

In a further embodiment, $R^1$ and $R^2$ are preferably each independently a C13 to C19, in particular a C13 to C17 functional group. Most preferably, $R^1$ and $R^2$ are independently a linear saturated C13-, C15- or C17-alkyl functional group.

n is preferably an integer from 2 to 10 and most preferably 2 or 3.

The stimuli-sensitive nanocarrier systems, in particular thermosensitive liposomes, particularly preferably comprise at least one phosphatidyldiglycerol and/or at least one phosphatidyltriglycerol. It has been found that such stimuli-sensitive nanocarrier systems, in particular liposomes, comprising diglycerols and/or triglycerols exhibit particularly advantageous release behaviour.

According to the invention, stimuli-sensitive nanocarrier systems, in particular liposomes, in which in each case only a single isomer of a phosphatidyloligoglycerol compound is present, for example only 1,2-dipalmitoylphosphooligoglycerol and not 1,3-dipalmitoylphosphooligoglycerol, are preferable.

The stimuli-sensitive nanocarrier system, in particular thermosensitive liposome, preferably comprises a stereospecific phosphatidyloligoglycerol of formula (IIa)

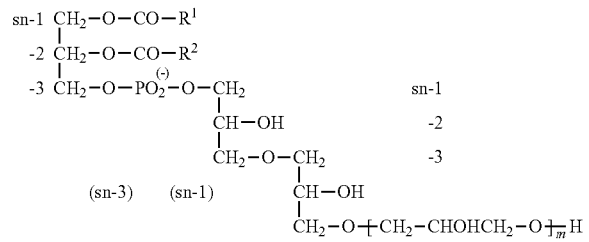

wherein $R^1$ and $R^2$ each independently represent a hydrocarbon functional group having from 12 to 24 carbon atoms and m is an integer from 0 to 50, wherein the linkage from the glyceride to the phosphate group is stereospecific and is in the form of an sn-3 linkage and the linkage from the phosphate group to the oligoglycerol is stereospecific and is in the form of an sn-1 linkage.

m is preferably from 0 to 8 and most preferably 0 or 1.

A stereospecific phosphatidyldiglycerol is particularly preferable

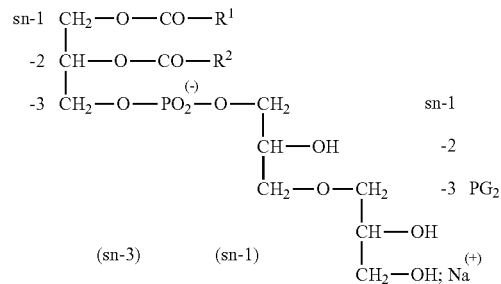

Configuration: natural
Name: 1,2-diacyl-sn-3-glycero-phospho-sn-1-diglycerol; sodium salt (correspondingly also oligoglycerols, in particular tri- or tetra-glycerols)
$R_1$, $R_2$, fatty acids; sn, stereospecific numbering;
$PG_2$, phosphodiglycerol
wherein $R^1$ and $R^2$ each independently represent a hydrocarbon functional group having from 12 to 24 carbon atoms.

$R^1$ and $R^2$ are preferably each independently of the other a preferably linear saturated or mono- or poly-unsaturated alkyl functional group, in particular a saturated alkyl functional group. $R^1$ and $R^2$ are further preferably each independently a C14 to C20, in particular a C14 to C18 functional group.

Preferably, $R^1$ and $R^2$ are each independently a linear saturated C12- to C24-, in particular C12- to C20-alkyl functional group.

Most preferably, $R^1$ and $R^2$ are independently a linear saturated C14-, C16- or C18-alkyl functional group.

In a further embodiment, $R^1$ and $R^2$ are preferably each independently a C13 to C19, in particular a C13 to C17 functional group. Most preferably, $R^1$ and $R^2$ are independently a linear saturated C13-, C15- or C17-alkyl functional group.

1,2-Dipalmitoyl-sn-3-glycero-phospho-sn-1-diglycerol is most preferable.

The configuration of the phospholipids is not important for the physical properties of the stimuli-sensitive nanocarrier systems, in particular liposomes, that is to say the physical properties do not change even if racemates or 1,3-diacylglycerols occur in the structure. They are, however, less preferable for other reasons, because they cannot be degraded or can be degraded to only a limited extent by phospholipases. This is particularly true for the phospholipases A, B, C and D, which are responsible for the degradation of the phospholipids. Hitherto, no research at all has been carried out into whether 1,3-dipalmitoyl-glycero-2-phospholipids, for example, can be degraded metabolically. In other words, the question of whether such phospholipids accumulate in the organism, and can even be toxic, remains unanswered.

Prior to clinical use, it must therefore be ensured that the phospholipids used have a defined structure—defined in terms of structure, fatty acid composition and configuration. Otherwise, it would have to be alternatively shown in long-term studies (animal experiments) that non-natural phospholipids in terms of structure and configuration do not have toxic properties, because clinical use, in particular in the indication of cancer, means that the therapy must be carried out for a prolonged period.

It is therefore particularly preferable that the phospholipids used are uniform and natural in terms of structure, configuration and fatty acid composition. Preferably, only 1,2-diacyl-sn-glycero-3-phosphocholines and 1,2-diacyl-sn-glycero-3-phospho-sn-1-di-, -tri- or -tetra-glycerols are used.

This means that the nanocarrier systems according to the invention in particular do not comprise 1,3-diacyl-glycero-3-phosphocholines and 1,2-diacyl-glycero-3-phospho-oligoglycerols (oligo ≙ from 2 to 50, in particular from 2 to 10 glycerol units).

According to the invention, in particular stereospecific lipids are provided or used. By means of previous preparation processes, in which 1,2-diacylglycerol, for example 1,2-dipalmitoylglycerol, was mostly used as the starting product for the phosphorylation, phosphatidyloligoglycerols of very good quality (purity >99%) could be obtained. However, it was then found that the structural purity was only in the region of ~90%; that is to say, a fatty acid migration from the 2-position to the 3-position occurred during the phosphorylation or in part also during storage of 1,2-diacyl-glycerol, for example 1,2-dipalmitoyl-glycerol. 1,3-Diacyl-glycerol, for example 1,3-dipalmitoyl-glycerol, formed, at least to an extent of approximately 10%. The diacyl-glycerol, for example 1,3-dipalmitoyl-glycerol, formed by fatty acid migration is likewise phosphorylated and converted into 1,3-dipalmitoyl-2-phospho-oligo-glycerol. The physical properties of the 1,2- or 1,3-derivative are very similar, so that purification by chromatography is possible but complex.

The novel processes avoid the use of 1,2-diacyl-glycerol, for example 1,2-dipalmitoylglycerol, by using a completely novel protecting group system which is specifically directed at preparing phosphatidyl-oligo-glycerols in chemically analytically pure and structurally pure form and in a natural configuration. The structural units necessary therefor are described herein.

The novel synthesis routes have the advantage that the structural units used are absolutely stable under the reaction conditions. No decomposition or migration of substituents in the molecule occurs.

A further advantage of the novel processes is, however, that the fatty acid composition is not specified from the outset via the diacylglycerols that are used. This leads to separate synthesis and phosphorylation steps for each fatty acid pattern that is desired.

In the novel processes, the separate and complex preparation of the 1,2-diacylglycerols, for example of 1,2-dipalmitoyl-glycerol, is further omitted. The two free hydroxyl groups are freed from the isopropylidene-glycerol functional group only at the end of the synthesis. A plurality of fatty acid derivatives can then be prepared by simple acylation, for example using palmitic acid chloride or other fatty acid chlorides. The benzyl protecting groups are then removed, as is conventional, by catalytic hydrogenolysis in the presence of PD-C. After cleavage of the methyl protecting group using lithium bromide, the end product is obtained.

The physical properties of the stimuli-sensitive nanocarrier systems, in particular liposomes, according to the invention are specified by the fatty acid composition, which ensures precisely accurate thermosensitivity. Serum stability and biological degradation of the carrier systems, on the other hand, require a defined configuration. This can be achieved only by chemical synthesis but not by transesterification with phospholipase D.

The phosphatidyl-oligo-glycerols that are used lead to a long circulation time of the stimuli-sensitive nanocarrier systems, in particular liposomes, in the blood. The fatty acid composition ensures release of the active ingredients at a specific temperature and serum stability. Also preferable are molecules which ensure normal biological degradation, that is to say the molecules are preferably in the natural configuration and are degradable by phospholipases, for example by phospholipases A, B and C.

Preferable phosphatidyloligoglycerols which possess these properties are uniform in their configuration and are present in the natural configuration (see general formula IIa).

The amount of phosphatidyloligoglycerol is preferably at least 1 wt. %, more preferably at least 10 wt. % and yet more preferably at least 15 wt. %, and up to 70 wt. %, more preferably up to 50 wt. % and yet more preferably up to 30 wt. %, based on the total weight of the nanocarrier systems, in particular liposomes.

The nanocarrier systems, in particular liposomes, according to the invention can also comprise phosphatidylglyceroglycols, preferably phosphatidylglyceroglycols of formula (IV)

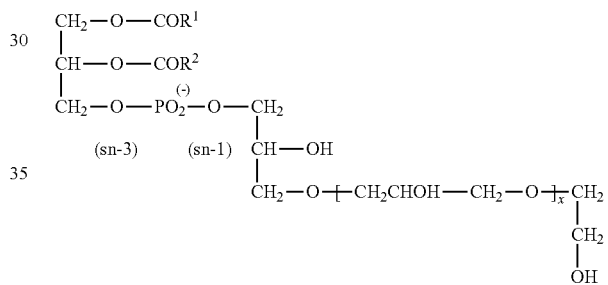

wherein $R^1$ and $R^2$ each independently represent a hydrocarbon functional group having from 12 to 24 carbon atoms and x is an integer from 0 to 50.

$R^1$ and $R^2$ are preferably each independently of the other a preferably linear saturated or mono- or poly-unsaturated alkyl functional group, in particular a saturated alkyl functional group. $R^1$ and $R^2$ are further preferably each independently a C14 to C20, in particular a C14 to C18 functional group.

Preferably, $R^1$ and $R^2$ are each independently a linear saturated C12- to C24-, in particular C12- to C20-alkyl functional group.

Most preferably, $R^1$ and $R^2$ are independently a linear saturated C14-, C16- or C18-alkyl functional group.

In a further embodiment. $R^1$ and $R^2$ are preferably each independently a C13 to C19, in particular a C13 to C17 functional group. Most preferably, $R^1$ and $R^2$ are independently a linear saturated C13-, C15- or C17-alkyl functional group, x is preferably an integer from 0 to 10, in particular 0, 1, 2 or 3.

The nanocarrier systems, in particular liposomes, according to the invention can also comprise a cardiolipin, preferably cardiolipins of formula (V)

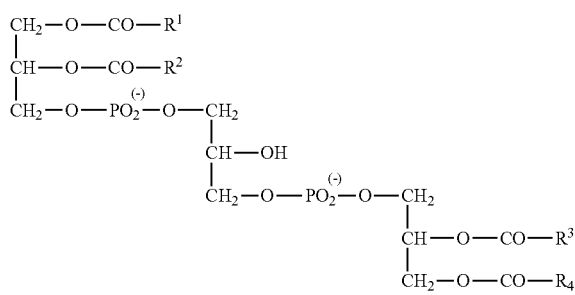

wherein $R^1$, $R^2$, $R^3$ and $R^4$ each independently represent a hydrocarbon functional group having from 12 to 24 carbon atoms and x is an integer from 0 to 50.

$R^1$, $R^2$, $R^3$ and $R^4$ are preferably each independently of the other a preferably linear saturated or mono- or poly-unsaturated alkyl functional group, in particular a saturated alkyl functional group. $R^1$, $R^2$, $R^3$ and $R^4$ are further preferably each independently a C14 to C20, in particular a C14 to C18 functional group.

Preferably, $R^1$ and $R^2$ are each independently a linear saturated C12- to C24-, in particular C12- to C20-alkyl functional group.

Most preferably, $R^1$, $R^2$, $R^3$ and $R^4$ are independently a linear saturated C14-, C16- or C18-alkyl functional group.

In a further embodiment, $R^1$, $R^2$, $R^3$ and $R^4$ are preferably each independently a C13 to C19, in particular a C13 to C17 functional group. Most preferably, $R^1$, $R^2$, $R^3$ and $R^4$ are independently a linear saturated C13-, C15- or C17-alkyl functional group.

Cardiolipins increase the circulation time of nanocarrier systems, in particular of liposomes, in the blood, Stimuli-sensitive nanocarrier systems, in particular thermosensitive liposomes, which are stable, that is to say do not release any active ingredient, in serum at 37° C. are preferable. At 42° C., however, the active ingredient is released rapidly within a period of <15 seconds.

The release of the active ingredients enclosed in the liposomes can take place, for example, in a targeted manner in the bladder wall, so that the active ingredient, in particular a cytostatic, can be released directly at the desired site.

For use of these stimuli-sensitive nanocarrier systems, in particular liposomes, for the targeted therapy of localised tumours, firstly the physical properties of the stimuli-sensitive nanocarrier systems, in particular liposomes, are of critical importance. The framework conditions are set by the body temperature of 37° C. in a healthy human being. The stimuli-sensitive nanocarrier systems, in particular liposomes, loaded with active ingredient should be stable at 36 to 37° C. In the event of a local increase in the temperature in the tumour region to 42° C., the active ingredient should be released rapidly, in <15 seconds. The stimuli-sensitive nanocarrier systems, in particular liposomes, can preferably be prepared by means of suitable phospholipids which are based on fatty acid esters having a chain length of from $C_{14}$ to $C_{18}$ (myristic acid, palmitic acid, stearic acid; see in this connection also Table 1). These phospholipids pass through a phase transition temperature in the region of about 40° C. Below 40° C., the phospholipids arranged in a lamellar manner are in the crystalline phase; above that temperature they are in the fluid phase. In the transition region in a narrow temperature range between 40 and 42° C., the active ingredients are spontaneously released.

The main transition temperature for (1,2-dipalmitoyl)-phosphatidylcholine is approximately 41° C. The purely physical requirements for clinical use in liposomes can accordingly be fulfilled by this phosphatidylcholine. However, the serum stability in the bloodstream of humans and animals that is required for clinical applications is lacking. (1,2-Dipalmitoyl)phosphatidylcholine alone is therefore not sufficient to achieve the therapeutic aims. Therefore, the intended therapy aims cannot be achieved by (dipalmitoyl) phosphatidylcholine alone.

However, by using phosphatidyloligoglycerols it has been possible to prepare stimuli-sensitive nanocarrier systems, in particular thermosensitive liposomes, having a prolonged circulation time in the blood simply by adding phosphatidyldiglycerol or phosphatidyltriglycerol. Simple addition is possible because phosphatidylcholines, phosphatidyldiglycerols or phosphatidyltriglycerols, having the same structure and the same fatty acid distribution in the glycerol molecule, have comparable phase transition temperatures, for example approximately 41° C. for the corresponding dipalmitoyl compounds.

A further important point is that phosphatidylcholines and phosphatidyloligoglycerols yield ideal mixtures without phase separation, provided that the length of the fatty acids does not differ by >4 $CH_2$ groups. This is an important prerequisite if it is to be possible to set phase transition temperatures between 23° C. (pure dimyristoyl-phosphatidylcholine) and 41° C. (pure dipalmitoyl-phosphatidylcholine) as desired, likewise between 41° C. and 56° C. (pure distearoylphosphatidylcholine). Phosphatidyloligoglycerols can correspondingly also be used in these mixtures.

In one embodiment, stimuli-sensitive nanocarrier systems, in particular thermosensitive liposomes, having a main phase transition temperature of approximately from 40° C. to 42° C. are formed from mixtures of (dipalmitoyl)-phosphatidylcholine, (distearoyl)-phosphatidylcholine and (dipalmitoyl)-phosphatidyl-di- or -tri-glycerol, that is to say three-component systems. The 1,2-dipalmitoylphosphatidylcholine serves as the basic matrix for setting the phase transition temperature at approximately 42° C., the 1,2-distearoylphosphatidylcholine leads to a slight increase in the phase transition temperature, and (1,2-dipalmitoyl)-phosphatidyl-di- or -tri-glycerol serves to establish serum stability and stability in the bloodstream.

Systems comprising from 40 to 60 wt. % 1,2-dipalmitoylphosphatidylcholine, from 15 to 25 wt. % 1,2-distearoylphosphatidylcholine and from 20 to 40 wt. % 1,2-dipalmitoylphosphatidyldiglycerol are preferable. The constituents are yet more preferably each used in stereospecific form.

In a further preferred embodiment, a two-component system of (1,2-dipalmitoyl)phosphatidylcholine and (1,2-distearoyl)-phosphatidyl-di- or -tri-glycerol is also sufficient.

By using stimuli-sensitive nanocarrier systems, in particular thermosensitive liposomes, according to the invention, an active ingredient enclosed in the stimuli-sensitive nanocarrier systems, in particular liposomes, can be released by exerting a stimulus, in particular local heating of the stimuli-sensitive nanocarrier systems, in particular liposomes. The stimuli-sensitive nanocarrier systems, in particular thermosensitive liposomes, are therefore particularly suitable for the local therapy of tumours, in particular of bladder tumours, or bladder carcinomas. The release of the active ingredient enclosed in the stimuli-sensitive nanocarrier systems, in particular liposomes, can be induced in a targeted manner in the bladder wall, so that the active ingredient, in particular a cytostatic, can be released directly at the desired site. These experiences can also be used for the therapy of other solid and localised tumours.

The stimuli-sensitive nanocarrier systems, in particular liposomes, described herein are particularly suitable for the local release of active ingredients by hyperthermia. Stimuli-sensitive nanocarrier systems, in particular liposomes, that are thermosensitive and comprise at least one phosphatidylcholine and at least one phosphatidyloligoglycerol having a phase transition temperature in each case of about 40° C. are preferable. This means that preferably myristic acid, palmitic acid or stearic acid esters are suitable as fatty acid esters. Other phase transition temperatures can of course also be set via corresponding fatty acid esters (see in this connection also Table 1).

It has been found that stimuli-sensitive nanocarrier systems, in particular thermosensitive liposomes, that comprise at least one phosphatidylcholine and at least one phosphatidyldiglycerol or phosphatidyltriglycerol having phase transition temperatures of about 40° C. have long half-lives at normal temperatures of about 36 to 37° C. in the bloodstream of experimental animals. Enclosed active ingredients are only released when the temperature is increased locally to about 42° C.

The stimuli-sensitive nanocarrier system, in particular thermosensitive liposome, claimed according to the invention preferably comprises at least one phosphatidylcholine and at least one phosphatidyl-di-, -tri- or -tetra-glycerol. The phase transition temperature is governed by the requirements of the application. It is preferably set at approximately 42° C. for clinical applications, which is achieved in a simple manner by means of the possible fatty acid combinations in the glycerol molecule (see in this connection also Table 1). For other applications, different phase transition temperatures below 40° C. may be of interest, for example temperatures of about <30° C., which can again be achieved via corresponding fatty acid combinations (see Table 1). Such stimuli-sensitive nanocarrier systems, in particular liposomes, are of interest because, when injected directly into the tumour region, they release their active ingredient immediately in the tumour tissue. Correspondingly, stimuli-sensitive nanocarrier systems, in particular liposomes, having higher phase transition temperatures are also important because such stimuli-sensitive nanocarrier systems, in particular liposomes, are very stable and do not release the active ingredient directly but are able to release the active ingredient slowly after being taken up into cells, for example, without a thermal effect being necessary. Therefore, there are stimuli-sensitive nanocarrier systems, in particular liposomes, which are still stable even at 50° C. or more.

A distinction can be made between three preferred embodiments of these stimuli-sensitive nanocarrier systems, in particular liposomes:

1) Preferred
   The liposome composed of phospholipids comprises at least one phosphatidylcholine and at least one phosphatidyloligoglycerol. The fatty acid chains are selected such that a phase transition temperature of approximately 42° C. is achieved. The position of the fatty acid chains in the glycerol molecule and the position of the phosphate functional group are arbitrary—it is the phase transition temperature of approximately 42° C. that is important for therapeutic use in vivo, which can usually be achieved with fatty acid esters having a chain length of $C_{14}$ to $C_{18}$ (myristic acid, palmitic and stearic acid).

2) More preferable
   This category includes liposomes having 1,2-diacyl-sn-3-glycero-phospho-rac-oligoglycerols.
   None of the physical properties, such as phase transition temperature, ideal mixing behaviour, change. However, these molecules do not occur naturally and are therefore not metabolised or degraded or are metabolised or degraded only slowly.

3) Yet more preferable
   This category includes liposomes of phospholipids having a natural configuration: sn-glycero-3-phosphoric acid ester sn-1-phospho-di-, -tri- or -tetra-glycerols. All the physical properties, such as phase transition temperature, ideal mixing behaviour, are unchanged. The configuration is natural, that is to say biological degradation of the molecules is ensured.

By selecting a phosphatidylcholine having a suitable main transition temperature, the stimuli-sensitive nanocarrier system, in particular thermosensitive liposome, can be customised. Table 1 gives main transition temperatures ($T_M$) of phosphatidylcholines whose main transition temperatures are in the range of from 0 to 80° C. As can be seen from the table, the main transition temperatures are dependent on the chain length and on the distribution over positions 1 and 2 of glycero-3-phosphocholine or over positions 1 and 3 of glycero-2-phosphocholine.

The phosphatidylcholine is present in the stimuli-sensitive nanocarrier systems, in particular liposomes, preferably in an amount of at least 10 wt. %, more preferably in an amount of at least 30 wt. %, yet more preferably in an amount of at least 50 wt. %, but not more than 90 wt. %.

Very generally, the phase transition temperature of the phosphatidylcholines can be controlled via the chain length of the fatty acid esters, as is shown by Table 1. The main transition temperature ($T_M$) of the phosphatidylcholines can be customised to the particular requirement. For clinical applications, temperatures of about 40° C. are of particular importance.

In addition to the purely physical properties of the stimuli-sensitive nanocarrier systems, in particular liposomes, that is to say stability at 37° C. but release of the active ingredient at 42° C. in physiological saline solution, the stimuli-sensitive nanocarrier systems, in particular liposomes, can, however, be used therapeutically only if those requirements are also met in the presence of serum and also in model experiments in experimental animals. That stability can in principle not be achieved if liposomes of (dipalmitoyl)-phosphatidylcholine and (dipalmitoyl)-phosphatidylglycerol are used. In this system, animal experiments show that the contents of the liposomes, the active ingredient, are released almost completely in <one minute.

The requirements necessary for clinical use, that is to say stability at 37° C. but release of the active ingredient at 42° C., could be achieved in animal experiments only using novel negative charge carriers, the phosphatidyloligoglycerols, in particular the phosphatidyldiglycerols and phosphatidyltriglycerols.

For clinical use, a further point must, however, be taken into consideration. According to the invention, phosphatidyldiglycerols and phosphatidyltriglycerols having phosphoric acid esters which have an sn-1 linkage and thus the naturally occurring configuration have been prepared for the first time.

Therefore, the present application also provides stereo-specific phosphatidyloligoglycerols of formula IIa

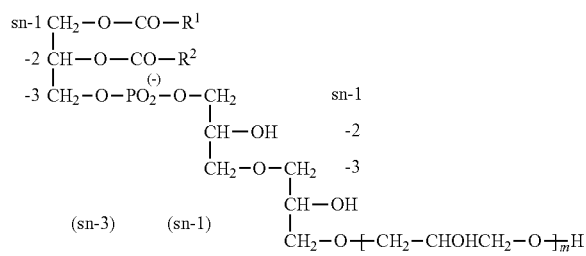

Configuration: natural
Name: 1,2-diacyl-sn-3-glycero-phospho-sn-1-oligoglycerol;
sn, stereospecific numbering;
wherein $R^1$ and $R^2$ each independently represent a hydrocarbon functional group having from 12 to 24 carbon atoms and m is an integer from 0 to 50, wherein the linkage from the glyceride to the phosphate group is stereospecific and is in the form of an sn-3 linkage and the linkage from the phosphate group to the oligoglycerol is stereospecific and is in the form of an sn-1 linkage.

$R^1$ and $R^2$ are preferably each independently of the other a preferably linear saturated or mono- or poly-unsaturated alkyl functional group, in particular a saturated alkyl functional group. $R^1$ and $R^2$ are further preferably each independently a C14 to C20 in particular a C14 to C18 functional group.

Preferably, $R^1$ and $R^2$ are each independently a linear saturated C12- to C24-, in particular C12- to C20-alkyl functional group.

Most preferably, $R^1$ and $R^2$ are independently a linear saturated C14-, C16- or C18-alkyl functional group.

m is preferably an integer from 0 to 10 and most preferably 0 or 1.

In the case of a clinical application, for example in tumour therapies, the physiological tolerability is of great importance. The stimuli-sensitive nanocarrier system, in particular liposome, as the carrier system should be readily degradable by phospholipases after the active ingredient has been released. According to the invention, therefore, molecules that have a phosphoric acid sn-1 linkage to the glycerol structural units are most preferably used as phosphatidyl-diglycerols and analogues. The advantage is rapid degradation by phospholipases.

The fundamental requirements for a clinical application are thus met, in particular for use in the regional therapy of tumour diseases, for example bladder tumour. The effectiveness of these therapies has already been confirmed in animal experiments.

The stimuli-sensitive nanocarrier systems, in particular thermosensitive liposomes, according to the invention are preferably free of cholesterol, because cholesterol leads to a spreading-out of the phase transition temperature and thus to a broad thermal transition range. In particular, the stimuli-sensitive nanocarrier systems, in particular thermosensitive liposomes, according to the invention comprise cholesterol in an amount of <0.1 wt. %, more preferably <0.01 wt. %. Particularly preferably, the stimuli-sensitive nanocarrier systems, in particular liposomes, do not contain any cholesterol but are completely free of cholesterol.

According to a preferred embodiment, the stimuli-sensitive nanocarrier systems, in particular liposomes, according to the invention additionally comprise lesser amounts of alkylphosphocholines, preferably from 10 to 15 wt. %. Suitable substances are, for example, hexadecylphosphocholine, oleylphosphocholine and also ether lysolecithins. In the case of the ether lysolecithins, the hydroxyl group in position 2 of the glycerol can be methylated or can be free. In this embodiment, it is possible to increase the release of the substances enclosed in the liposome from approximately 70% without the content of alkylphosphocholine to virtually 100%, which is attributable to an acceleration of the opening of the stimuli-sensitive nanocarrier systems, in particular liposomes. Furthermore, the alkylphosphocholines exhibit an anti-tumour effect owing to temperature-dependent release from the stimuli-sensitive nanocarrier systems, in particular liposomes.

The stimuli-sensitive nanocarrier systems, in particular thermosensitive liposomes, according to the invention further preferably comprise an active ingredient, in particular an active ingredient suitable for the treatment of bladder tumours. The stimuli-sensitive nanocarrier systems, in particular liposomes, preferably comprise a cytostatic, in particular a cytostatic selected from the group consisting of mitomycin C, doxorubicin, epirubicin, gemcitabine, trabectedin, cisplatin, carboplatin and oxaliplatin.

The thermosenstivity of the liposomes according to the invention is determined by the phase transition of the phosphatidylcholines within the liposome membrane. If the phase transition temperature is passed through, the membrane briefly becomes unstable and the liposome contents are accordingly released. This effect is used according to the invention for treating bladder tumours. The bladder tumour is thereby heated regiospecifically, for example within the context of regional hyperthermia. The temperature in the tumour increases above the limit temperature for release of the liposome contents. The liposome contents are then released specifically and almost exclusively in the tumour, so that the active ingredients can be used effectively for treating the tumour.

The invention therefore further relates to a thermosensitive liposome as described herein in combination with hyperthermia and/or ultrasound. Heating can be effected in this case by a large number of methods, such as simply flushing the bladder with warm water, heating by means of electromagnetic waves, ultrasound or laser.

The stimuli-sensitive nanocarrier systems, in particular thermolabile liposomes, according to the invention are prepared in the conventional manner by dissolving the lipids, for example in chloroform or chloroform/water/isopropanol, removing the solvent, advantageously in vacuo in a rotary evaporator, tempering the lipids with aqueous solutions of the ingredients to be encapsulated at temperatures that are above the phase transition temperature. The duration of the tempering treatment is advantageously from 30 to 60 minutes but can also be shorter or longer. Homogenisation is carried out by repeated freeze/thawing processes, for example freezing and thawing again from 2 to 5 times. Finally, the lipid suspension obtained is extruded through a membrane of defined pore size at a temperature above the phase transition temperature in order to achieve the desired stimuli-sensitive nanocarrier system size (??), in particular liposome size. Suitable membranes are, for example, polycarbonate membranes of defined pore size, such as from 100 to 200 nm. Finally, any ingredients not encapsulated can be separated off, for example by column chromatography or the like.

The release of active ingredients in locoregional therapy is not limited to the treatment of bladder tumours.

The invention therefore also includes a stimuli-sensitive nanocarrier system, in particular thermosensitive liposome, for use in the treatment of other tumours, in particular soft-tissue sarcoma, osteosarcoma, bladder carcinoma (muscle invasive bladder cancer [MIBC] and non-muscle invasive bladder cancer [NMIBC]), ovarian carcinoma, stomach carcinoma, breast carcinoma (especially triple negative breast cancer [TNBC]), hepatocellular carcinoma, uterine carcinoma, carcinoma of the thyroid gland, head-neck tumours, prostate carcinoma, chordoma, desmoid tumour, glioblastoma and other tumour diseases having preferably locoregional spread.

Such nanocarrier systems preferably comprise an active ingredient suitable for treating the tumour in question, which is then released stimuli-sensitively in or in the vicinity of the tumour.

Suitable active ingredients for treating tumours are, for example, anthracyclines (for example doxorubicin, epirubicin), oxazaphosphorines (for example hydroxyifosfamide), platinum analogues (cisplatin, oxaliplatin, carboplatin), gemcitabine, 5-fluorouracil, paclitaxel, docetaxel, etoposide, topotecan, vincristine, irinotecan, methotrexate, bleomycin, tyrosine kinase inhibitors, small molecules, DNA therapeutics or radiosensitisers (in conjunction with radiotherapy).

Furthermore, the stimuli-sensitive nanocarrier systems according to the invention can be used in the treatment of infectious diseases, in particular infectious diseases caused by bacteria, viruses, fungi and/or parasites.

The treatment of infections of medical implants, in particular orthopaedic prostheses, the treatment of localised infections, in particular infections of the deep soft tissue and/or of bone, and/or the therapy of multiresistant pathogens is preferable.

To that end, the stimuli-sensitive nanocarrier systems, in particular thermosensitive liposomes, preferably comprise an active ingredient selected in particular from antibiotics, virostatics, fungicides, and medicinal drugs having an anti-parasitic effect. The active ingredient is particularly preferably selected from:

antibiotics, in particular β-lactams, glycopeptides, polyketides, aminoglycoside antibiotics, polypeptide antibiotics, quinolones, sulfonamides (for example linezolid, flucloxacillin, cefazolin, clindamycin, vancomycin, teicoplanin, rifampicin, ampicillin, ceftazidime, ceftriaxone, cefepime, piperacillin, fluoroquinolones, metronidazole, amikacin, etc.) and/or virostatics, in particular entry inhibitors, penetration inhibitors, DNA polymerase inhibitors, DNA/RNA polymerase inhibitors, reverse transcriptase inhibitors, inosine monophosphate dehydrogenase inhibitors, protease inhibitors, integrase inhibitors, helicase-primase inhibitors, cyclophilin inhibitors, maturation inhibitors, terminase inhibitors, neuraminidase inhibitors, etc., and/or fungicides, in particular azoles (benzimidazoles ("MBC"), triazoles, imidazoles), morpholines, strobilurins, quinolines, anilino-pyrimidines, oxazolidine-diones, carboxylic acid amides, etc.

The stimuli-sensitive nanocarrier systems, in particular thermosensitive liposomes, according to the invention can further be used in the treatment of diseases of the eye, in particular in the treatment of inflammatory, degenerative, infectious and/or neoplastic diseases of the eye, wound healing disorders and/or glaucoma.

In a further preferred embodiment, the stimuli-sensitive nanocarrier systems, in particular thermosensitive liposomes, can also be used in the treatment of autoimmune diseases, in particular in the treatment of rheumatoid arthritis and/or chronic inflammatory intestinal diseases. To that end, the stimuli-sensitive nanocarrier systems, in particular thermosensitive liposomes, preferably further comprise an active ingredient, in particular a steroid, TNF-α and/or immunosuppressants.

The invention also provides a stimuli-sensitive nanocarrier system, in particular thermosensitive liposome, for use in diagnosis, in particular for non-invasive temperature measurement using MR contrast agents and MR imaging. Such a stimuli-sensitive nanocarrier system, in particular thermosensitive liposome, preferably comprises as active ingredient a CT or MRT contrast agent, preferably selected from iodine-containing contrast agents or gadolinium chelates.

The stimuli-sensitive nanocarrier systems, in particular thermosensitive liposomes, according to the invention can further be used in the treatment of degenerative diseases, in particular for the localised release of anti-inflammatory agents, analgesics and/or chondroprotectants. Further fields of use of the stimuli-sensitive nanocarrier systems, in particular thermosensitive liposomes, are the treatment of dementia syndromes, Alzheimer's disease and/or focal neurological psychiatric diseases, in particular epilepsy, as well as the treatment of atherosclerosis.

For the treatment of thromboses, the stimuli-sensitive nanocarrier systems, in particular thermosensitive liposomes, preferably comprise at least one active ingredient selected from fibrinolytics, preferably streptokinase, urokinase and/or alteplase.

The invention will be explained further by the accompanying drawings and the following examples.

Example 1

The Synthesis of Phosphatidyl-Oligoglycerols
Important Structural Units
1) 3-Allyl-2-benzyl-sn-G (endogenous synthesis)
2) 1-Allyl-2-benzyl-sn-G (endogenous synthesis)
3) 1,2-Isopropylidene-sn-G (commercial product)
4) 2,3-Isopropylidene-sn-G (commercial product)

By means of these structural units, the desired phosphatidyloligoglycerols can be developed, having a natural or also a non-natural configuration. Hitherto, only racemic phosphatidyloligoglycerols have been prepared and tested in long-term circulating liposomes in this field.

Hitherto:

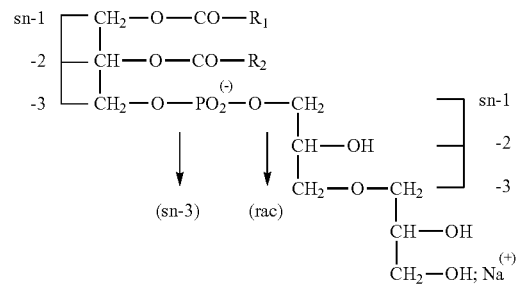

Configuration: racemic (non-natural)
Name: 1,2-diacyl-sn-3-glycero-phospho-rac-diglycerol
(correspondingly tri-OF tetra-glycerols)
Explanations: $R_1$, $R_2$—saturated alkyl functional groups;
sn stereospecific numbering;
rac—racemic linkage; correspondingly also tri- or tetra-glycerols According to the Invention:

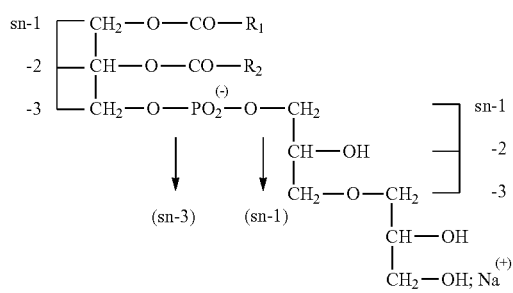

Configuration: natural
Name: 1,2-diacyl-sn-3-glycero-phospho-sn-1-diglycerol (correspondingly also tri- or tetra-glycerols)
Explanations: R1, R2—saturated alkyl functional groups; sn—stereospecific numbering;
diglycerols—correspondingly also tri- or tetra-glycerols The substances of natural configuration to the phosphate esters, that is to say (sn-3) linkage of diacylglycerol but (sn-1) linkage of the di-, tri- or tetra-glycerols, are described for the first time herein. They cannot be obtained from lecithins by transesterification with phospholipase D in the presence of glycerol, but only by targeted synthesis. The substances are in the natural configuration, that is to say (sn-3) and (sn-1) linkage.

In the preparation of the further substances too, such as
glycero-glycols
glycero-glycerols (branched)
glycero-glycero-glycols, synthesis routes have been developed which ensure that the substances contain a glycerol functional group which has an (sn-1) linkage of the phosphate ester to the phosphatidyloligoglycerol. These substances accordingly contain in the structure at least one glycerol molecule having a free OH group, which permits an (sn-1) linkage. The substances are novel, because an (sn-3) linkage of the diacyl-glycerolphosphoric acid ester and an (sn-1) linkage to the glycerol-glycol is possible here too. In addition, the structure here is also novel, because the terminal group is not glycerol but glycol or the like.

Example 2

Examples of the Synthesis of Phosphatidyl-Oligoglycerols Having Uniform and Natural Configuration Abbreviations used; P, palmitic acid; O, oleic acid; S, stearic acid; L, lauric acid; B, behenic acid; M, myristic acid; A, arachidic acid; Li, linoceric acid, PC, phosphocholine; $PG_2$, phosphodiglycerol; $PG_3$, phosphotriglycerol; $PG_4$, phosphotetraglycerol, Diglycerols
1) 1P-2M-sn-G-3-$PO_4^{(-)}$-sn-1-$G_2$;$Na^{(+)}$  TM ~27° C.
2) 1S-2M-sn-G-3-$PO_4^{(-)}$-sn-1-$G_2$;$Na^{(+)}$  TM ~33° C.
3) 1P-2P-sn-G-3-$PO_4^{(-)}$-sn-1-$G_2$;$Na^{(+)}$  TM ~41° C.
4) 1S-2P-sn-G-3-$PO_4^{(-)}$-sn-1-$G_2$;$Na^{(+)}$  TM ~48° C.
5) 1S-2S-sn-G-3-$PO_4^{(-)}$-sn-1-$G_2$;$Na^{(+)}$  TM ~27° C.

Triglycerols
1) 1S-2M-sn-G-3-$PO_4^{(-)}$-sn-1-$G_3$;$Na^{(+)}$  TM ~33° C.
2) 1P-2P-sn-G-3-$PO_4^{(-)}$-sn-1-$G_3$;$Na^{(+)}$  TM ~41° C.
3) 1S-2P-sn-G-3-$PO_4^{(-)}$-sn-1-$G_3$;$Na^{(+)}$  TM ~48° C.

Tetraglycerols
1) 1S-2M-sn-G-3-$PO_4^{(-)}$-sn-1-$G_4$;$Na^{(+)}$  TM ~33° C.
2) 1P-2P-sn-G-3-$PO_4^{(-)}$-sn-1-$G_4$;$Na^{(+)}$  TM ~41° C.
3) 1S-2P-sn-G-3-$PO_4^{(-)}$-sn-1-$G_4$;$Na^{(+)}$  TM ~48° C.
4) 1S-2S-sn-G-3-$PO_4^{(-)}$-sn-1-$G_4$;$Na^{(+)}$  TM ~48° C.

Example 3

Examples of the Synthesis of Phosphatidyl-Sn-1-Glycero Compounds of Natural Configuration (Novelty Through Structural Variation as Well as Through Uniform and Natural Configuration)

Glycero-glycols (G-Gly)
Structure:

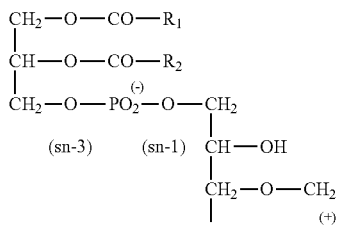

1) 1P-2P-sn-G-3-$PO_4^{(-)}$-(sn-1)-G-Gly; $Na^{(+)}$
2) 1S-2S-sn-G-3-$PO_4^{(-)}$-(sn-1)-G-Gly; $Na^{(+)}$

Glycero-glycerols (branched)
Structure:

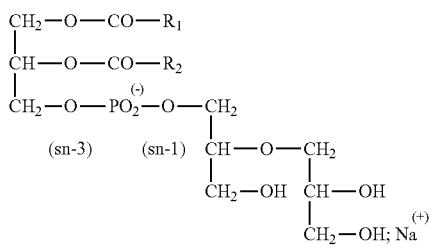

1) 1P-2P-(sn-3)-G-$PO_4^{(-)}$-(sn-1)-G-G; $Na^{(+)}$ (branched)
2) 1S-2S-(sn-3)-G-$PO_4^{(-)}$-(sn-1)-G-G; $Na^{(+)}$ (branched)

Diglycero-glycos (G$_2$-Gly)
Structure:

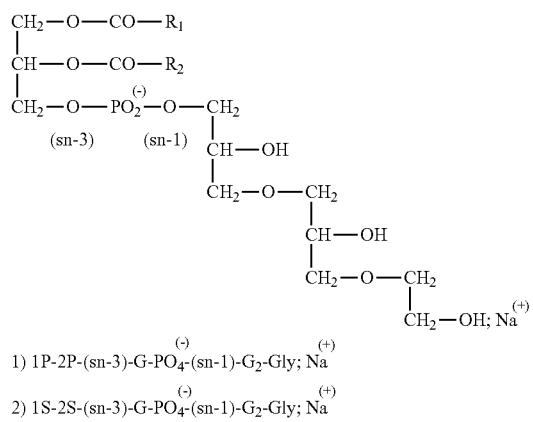

1) 1P-2P-(sn-3)-G-PO$_4$-(sn-1)-G$_2$-Gly; Na$^{(+)}$ (with (-) on PO$_4$)

2) 1S-2S-(sn-3)-G-PO$_4$-(sn-1)-G$_2$-Gly; Na$^{(+)}$ (with (-) on PO$_4$)

Example 4

Use of Thermosensitive Liposomes in the Treatment of Bladder Carcinoma

Thermosensitive liposomes according to the invention comprising 30 mol. % dipalmitoylphosphatidyldiglycerol or dipalmitoylphosphatidyltriglycerol were used.

FIG. 1 shows the principle of the intravascular active-ingredient release from thermosensitive liposomes.

Active-ingredient release generally occurs by passive transfer across the lipid membrane owing to a concentration gradient. At their phase transition temperature ($T_m$), phospholipids transition from a solid gel phase ($L_\beta$) to a liquid disordered phase ($L_\alpha$). The $L_\alpha$ phase is characterised by greater permeability compared with the $L_\beta$ phase. The permeability is greatest at temperatures close to the phase transition temperature $T_m$ owing to the coexistence of membrane regions in which both phases occur, whereby boundary regions having packing defects occur. The thermosensitive liposomes according to the invention release their contents into the bloodstream when they pass through heated tissue. A high rate of active-ingredient release is thereby provided.

In vivo experiments were carried out on female F344 rats weighing from 170 to 200 g which had developed an orthotopic bladder cancer through inoculation with AY27 cells. Pharmacokinetics and accumulation of doxorubicin (Dox) were evaluated by HPLC measurements. Focal tumour growth was initiated by chemical preconditioning of the bladder wall followed by AY27 cell instillation. Tumour growth was inspected by cystoscopy. TSL(Dox) (thermosensitive liposomes comprising doxorubicin) or free Dox were injected intravenously (i.v.) or introduced intravesically. Heating of the bladder was achieved by means of warm water.

Figure 2:
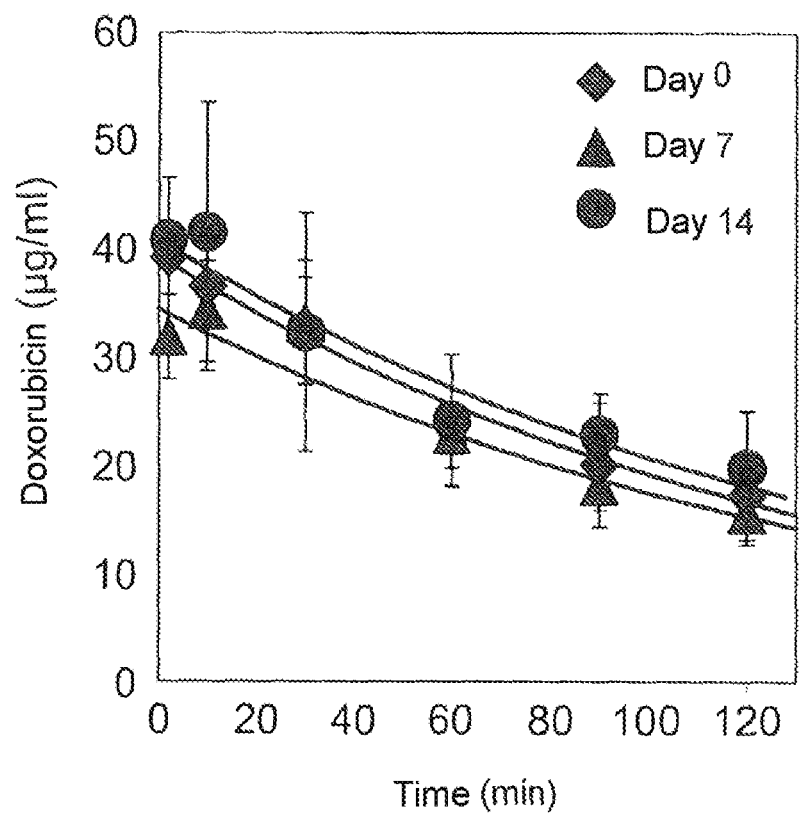

FIG. 2 shows the pharmacokinetic profile of TSL(Dox).

A TSL(Dox) administration of 2 mg/kg was carried out on female F344 rats on day 0 with a repeat administration after 7 or 14 days. TSL(Dox) exhibit high stability over 120 minutes.

Figure 3:
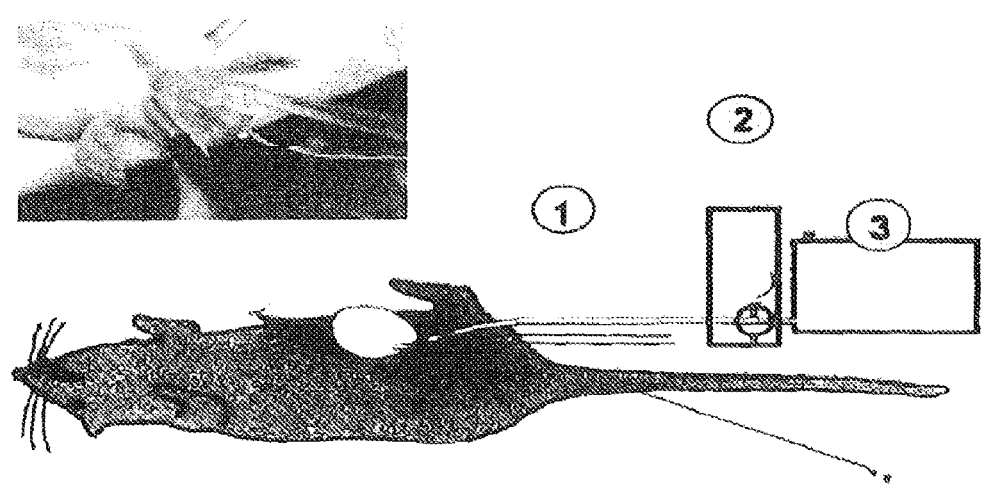

FIG. 3 shows the experimental design of the rat bladder carcinoma model (modified by Postius, Szelinyi; J. Pharmacol. Methods. 1983, 9: 53-61).

The rat is provided with two bladder catheters (1). A precision pump (2) transports heated water from the water bath (3) through one of the catheters into the bladder. The other catheter serves to discharge the warm water. When the temperature of the outgoing water reaches 41° C., thermosensitive liposomes comprising doxorubicin are injected into the tail vein and a one-hour hyperthermia treatment is started.

Figure 4:
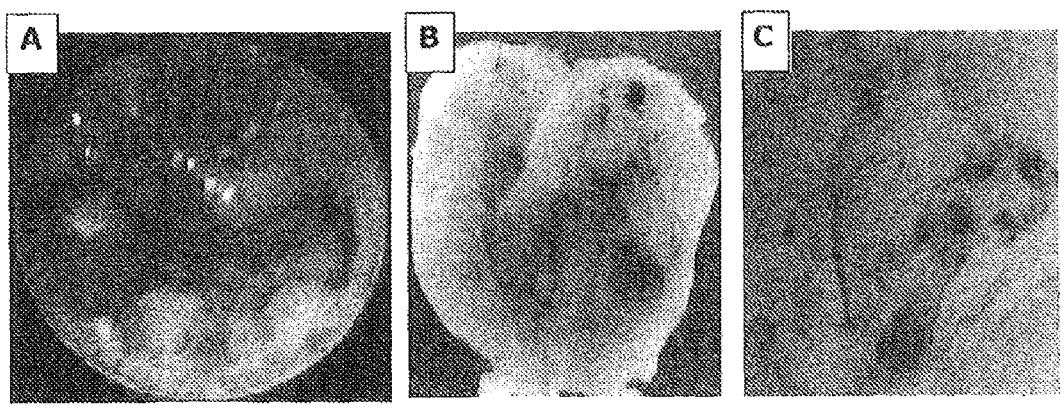

FIG. 4 shows a tumour macroscopy seven days after tumour cell inoculation.

The experiments were carried out on female F344 rats weighing from 170 to 200 g which had developed an orthoptic bladder cancer through inoculation with AY cells. Pharmacokinetics and accumulation of doxorubicin (Dox) was evaluated by HPLC measurements. Focal tumour growth was initiated by chemical preconditioning of the bladder wall followed by AY27 cell instillation. Multiple tumour plaque formations on the bladder wall were visualised by cytoscopy (A) and on a removed bladder (B and C).

Figure 5:
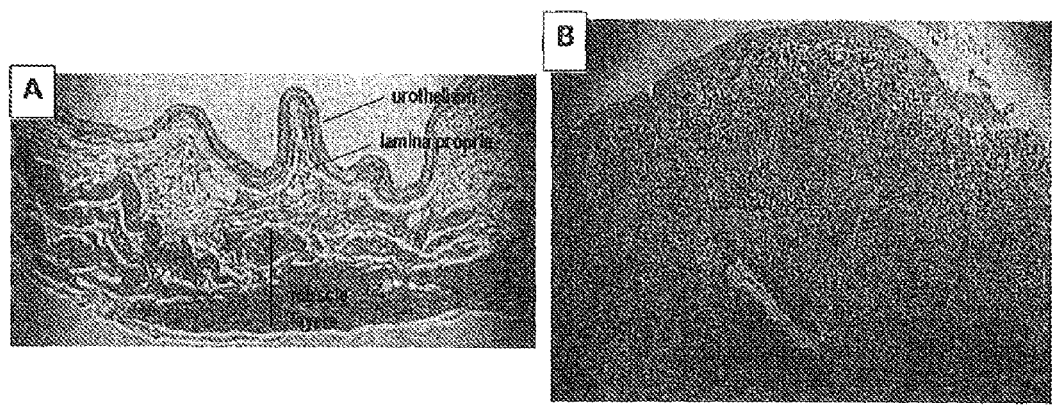

FIG. 5 shows the histology of a bladder.

FIG. (A) shows a bladder of normal appearance of an F344 rat at 10× magnification. FIG. (B) shows a pT1G3 tumour seven days after tumour cell inoculation, likewise at 10× magnification.

Figure 6:
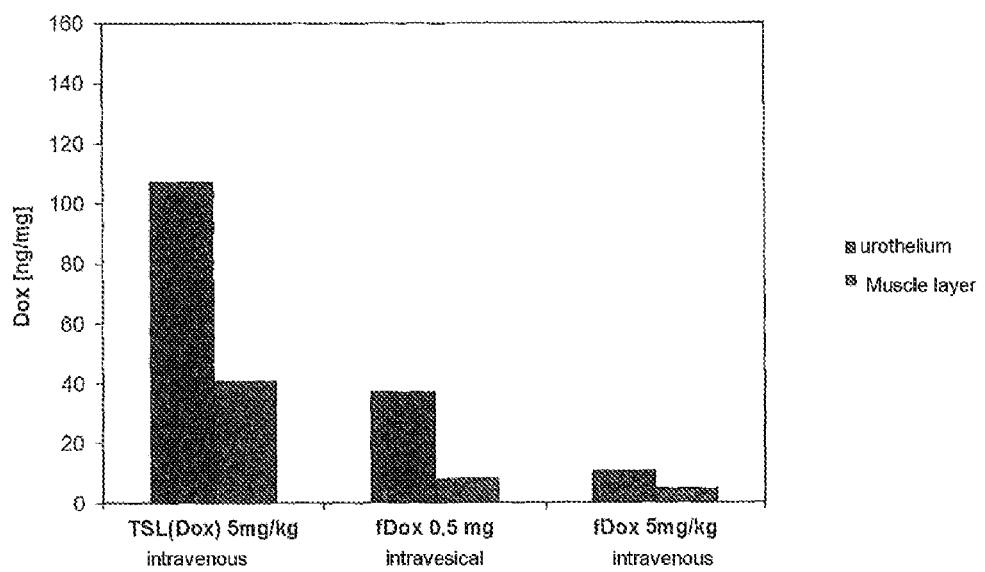

FIG. 6 shows tissue concentrations of Dox in the bladder wall of female F344 rats having a bladder tumour.

The figure shows the mean Dox concentration in the urothelium and in the muscle layer after treatment for one hour with intravenously administered TSL(Dox) and hyperthermia, intravesically administered free Dox (fDOX) and intravenously administered free Dox. The Dox dose for the i.v. treatment was 5 mg/kg body weight, and for the intravesical treatment it was 0.5 mg/rat. The Dox concentration in the urothelium was higher in all cases, regardless of the treatment procedure. The concentration in the urothelium/in the muscle layer of a tumour-bearing rat which had been treated with TSL(Dox)+hyperthermia was up to 3- to 5-times higher in comparison with intravesically administered free Dox.

Example 5

Important Structural Units for the Synthesis of Phosphatidyl-Diglycerols and Analogues A) (sn)-1,2-Isopropylideneglycerol is a commercial product having a free (sn)-3-hydroxyl group. It can be used directly

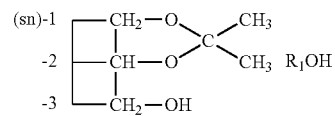

for phosphorylation. Phosphoric acid esters having (sn)-3 linkage are formed:

B) (sn)-3-Allylglycerol can be obtained from A by reaction with alkyl chloride and then by acidic cleavage of the isopropylidene protecting group. It serves to synthesise optically pure glycerol derivatives which have a free hydroxyl group in the (sn)-1 position.

C) (sn)-1-Trityl-2-benzyl-3-allyl-glycerol can be obtained from B by tritylation in (sn)-1 and subsequent benzylation in (sn-2).

D) (sn)-1-Trityl-2-benzyl-3-glycero-glycerol can be developed from C by epoxidation and ring opening.

E) (sn)-2-Benzyl-3-glycero-dibenzyl-glycerol can be prepared from D by dibenzylation and subsequent detritylation. There is formed an important structural unit which permits (sn)-1 linkage and thus the preparation of (sn)-1-phosphoric acid esters.

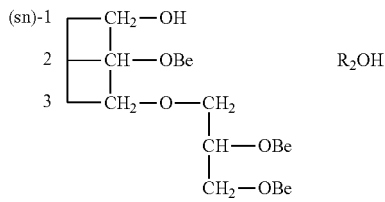

F) (sn)-1-OH-2-Benzyl-3-glycero-benzyl-glycol can be developed from D: vicinal diol cleavage using periodate and reduction of the aldehyde to the alcohol using sodium borohydride yields 1-trityl-2-benzyl-3-glycero-glycol. Benzylation of the free hydroxyl group and detritylation lead to the freeing of the (sn)-1 position, which can again be used for the preparation of (sn)-1-phosphoric acid esters.

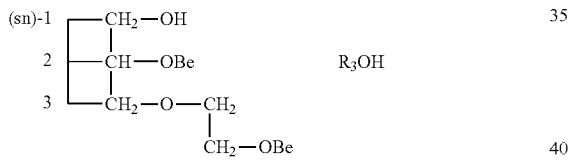

In a corresponding manner, (sn)-1-OH-2-benzyl-3-glycero-2-benzyl-glycero-benzyl-glycol can be developed from triglycerols using the same protecting group strategy:

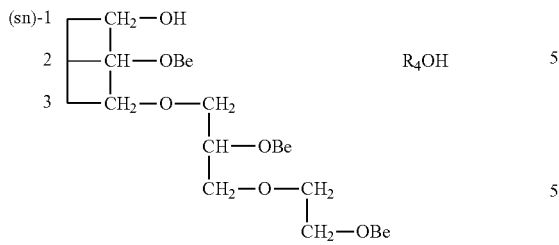

G) (sn)-1-Acetyl-2-benzyl-glycerol this protecting group is only used to prepare complex phospholipids such as cardiolipin, which contains two phosphoric acid esters in one molecule. The phosphatidyl functional groups present in the molecule are bonded together via a glycerol bridge. The above structural unit allows the production of this bridge as well as the preparation of the two phosphoric acid esters in the (sn)-3 position, that is to say likewise in the naturally occurring configuration.

G can be developed from structural unit C: detritylation in the (sn)-1 position, rearrangement of allyl to propenyl, acetylation of the (sn)-1 position and acidic cleavage of the propenyl protecting group yields structural unit G having a free (sn)-3 position:

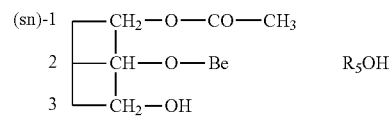

For the preparation of cardiolipins and analogues, particular measures must be taken because two negative charge carriers, that is to say two phosphate functional groups per molecule, are present in these molecules. To that end, the already phosphorylated functional group $R_5$ is used, after cleavage of the acetyl group, as the alcohol $R_6$ OH (see in this connection preparation of the phosphoric acid triesters: preparation of the phosphoric acid triester from $R_5OH$ and preparation of the phosphoric acid triester from $R_6OH$)

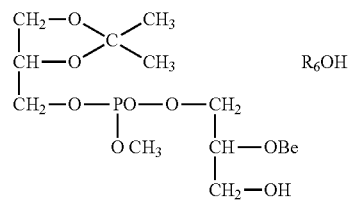

If $R_6OH$ is again reacted with phosphorus oxychloride, the diphosphate is obtained. The two phosphoric acid functional groups are then bonded together via a glycerol bridge.

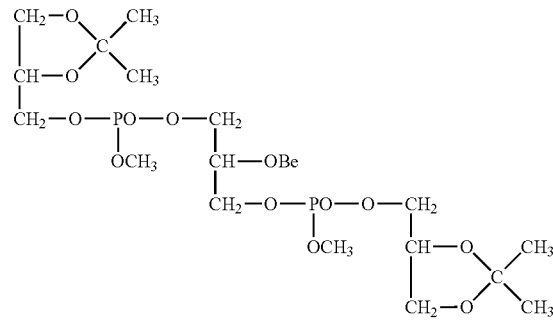

At the end of the synthesis, the four hydroxyl groups protected by isopropylidene are then freed. Acylation is then carried out, as is conventional, by known methods fatty acid chloride, for example palmitic acid chloride or palmitic acid. After cleavage of the benzyl ether protecting groups by catalytic hydrogenic hydrogenolysis with PD-C, the target product is obtained by cleavage of the methyl group using lithium bromide.

1-Acetylbropanediol-(1,3)

can likewise be used as the bridging molecule and then yields the deoxy-cardiolipins—likewise with other terminal diols such as glycol, (1,4)-butanediol, etc. These compounds are of lesser interest in our concept, which intends to use preferably naturally occurring phosphatidyl derivatives.

Example 6

Preparation of Strategically Important Phosphoric Acid Triesters by Stepwise Reaction of $POCl_3$ with Three Different, Primary Alcohols The preparation of defined, position-specific phosphoric acid triesters which are clear in terms of configuration has been researched intensively (see in this connection publications 1-10).

1) Eibl H. Synthesis of glycerophospholipids. Chem Phys Lipids. 1980 June; 26(4): 405-29
2) Eibl H. Phospholipid synthesis. In: Liposomes: From physical structure to therapeutic applications. Ed Knight C G, Elsevier, Amsterdam 1981; 19-50
3) Eibl H, Kovatchev S. Preparation of phospholipids and their analogs by phospholipase D. Methods Enzymol. Ed Löwenstein J M. 1981; 72: 632-9. Academic Press, New York
4) Eibl H. Phospholipide als funktionelle Bausteine biologischer Membranen. Angew Chem. 1984 (259): 9188-9198
5) Eibl H. Phospholipids as functional constituents of biomembranes. Angew Chem Int. Ed Engl 1984 (23) 257-271
6) Eibl H. Phospholipid synthesis: Oxazaphospholanes and dioxaphospholanes as intermediates. Proc Natl Acad Sci USA. 1978; 75: 4074-77
7) Eibl H, Woolley P. Synthesis of enantiomerically pure glyceryl esters and ethers. I. Methods employing the precursor 1,2-isopylidene-sn-glycerol. Chem Phys Lipids 1986 (41): 53-63
8) Eibl H, Woolley P. Synthesis of enantiomerically pure glyceryl esters and ethers. II. Methods employing the precursor 3,4-isopropylidene-D-mannitol. Chem Phys Lipids. 1988 (47): 47-53
9) Eibl H, Woolley P. A general synthetic method for enantiomerically pure ester and ether lysophospholipids. Chem Phys Lipid 1988 (47): 63-68
10) Woolley P. Eibl H. Synthesis of enantiomerically pure phospholipids including phosphatidylserine and phosphatidylglycerol. Chem Phys Lipids 1988 (47): 55-62

From the structural units described here, it is possible to prepare different phosphatidyl-oligo-glycerols and, correspondingly, phosphatidyl-glycero-glycols. It is particularly important that the fatty acid functional groups are prepared only at the end of the synthesis from a central intermediate, that is to say, unlike previous syntheses, the fatty acid functional groups are not introduced until the end. This is possible by preparing a central intermediate having two vicinal hydroxyl groups, for example

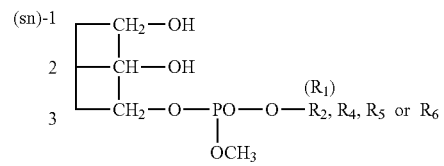

In German patent application 196 05 833.3 of 16 Feb. 1996 (inventor: H. Eibl; patentee: Max-Planck-Gesellschaft), the conditions for the stepwise esterification of phosphorus oxychloride using primary alcohols are discussed and described precisely. In contrast to the previous processes, in which 1,2-diacylglycerol, for example 1,2-dipalmitoylglycerol, was used in the first step (problem: fatty acid migration during the reaction or during storage of 1,2-dipalmitoylglycerol, which had to be prepared separately beforehand), the synthesis is initiated with (sn)-1,2-isopropylideneglycerol having a free sn-3 position, which can be obtained commercially. This saves the complex, separate synthesis of 1,2-diacylglycerol, for example 1,2-dipalmitoylglycerol, and the above-mentioned problems associated therewith.

Following these poor experiences with 1,2-dipalmitoylglycerol in the first phosphorylation step, the synthesis was carried out differently. The aim was to introduce the fatty acid esters only at the end of the synthesis via a freed vicinal diol. The following sequence of the synthesis steps is preferable:

$P_1$—first phosphorylation step with phosphorus oxychloride $R_1$ OH: (sn)-1,2-isopropylidene-glycerol (free sn-3 position)

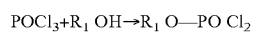

$P_2$—second phosphorylation step with $R_1$ O—PO $Cl_2$
$R_2$ OH or corresponding having free sn-1 position
$R_3$ OH; $R_4$ OH; $R_5$ OH; $R_6$ OH

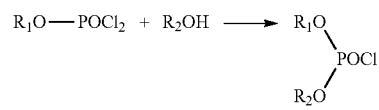

$P_3$—third phosphorylation step with

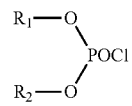

Methanolysis with $CH_3$ OH

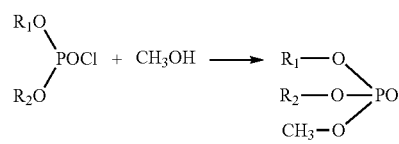

Furthermore, after phosphorylation using the benzyl-protected glycerols, the phosphoric acid diesters are not hydrolysed directly but are converted into phosphoric acid triesters by methanolysis. Freeing of the vicinal diol can then take place by acidic cleavage of the isopropylidene protecting group. The acylation of the hydroxyl groups is then carried out according to known methods (fatty acid chloride, for example palmitic acid chloride, or also free fatty acid).

The target products are then obtained by PD/C-catalysed hydrogenolysis followed by methyl cleavage using lithium bromide.

By way of example, some target products will be shown in graphic formulae, for example as dipalmitoyl esters:

Phosphatidyldiglycerols and Analogues

Phosphatidyl-diglycerols and phosphatidyl-triglycerols have been developed from phosphatidylglycerol, a naturally occurring membrane phospholipid. Surprisingly, the introduction of a further glycerol functional group which is linked via an ether bridge to phosphatidylglycerol leads to particular properties: The circulation times in the blood of liposomes comprising this phospholipid are changed and lengthened considerably.

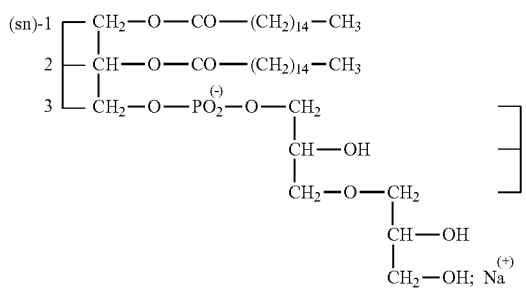

(sn)-1,2-Dipalmitoyl-glycero-3-phospho-sn-1-glycero-glycerol, sodium salt

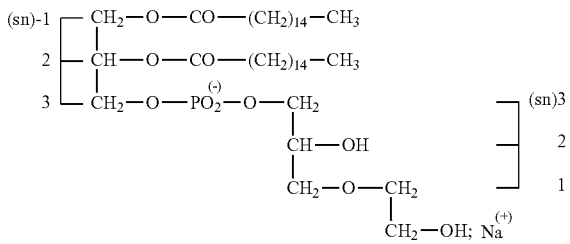

(sn)-1,2-Dipalmitoyl-sn-glycero-3-phospho-glycero-glycol, sodium salt

Cardiolipins and Structural Analogues

Cardiolipins and analogues, which likewise occur in natural membranes, also have properties that change the circulation time, and increase the circulation time of liposomes in the blood.

Using the structural units developed by us, it is also possible to prepare mixed-chain cardiolipins, that is to say, for example, also structures having only three fatty acid functional groups.

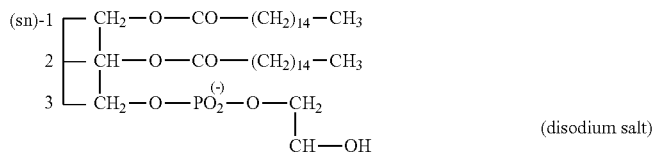

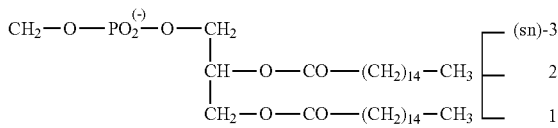

(disodium salt)

(Tetrapalmitoyl)-cardiolipin

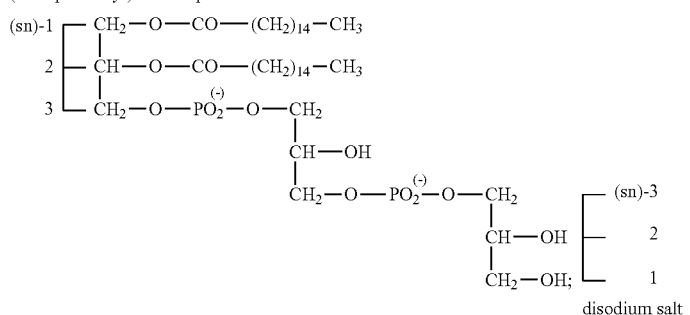

disodium salt (sn)-1,2-Dipalmitoyl-3-glycero-phospho-glycero-(sn)-3-phosphoglycerol, disodium salt 7. Examples of (sn)-1,2-diacyl-3-glycero-phospho-(sn)-1-diglycerol 1) Dipalmitoyl compound
sodium salt; $C_{41}H_{80}NaO_{12}P$ (MW 819.04)
2) Dimyristoyl compound
sodium salt; $C_{37}H_{72}NaO_{12}P$ (MW 762.93)
3) Distearoyl compound
sodium salt; $C_{45}H_{88}NaO_{12}P$ (MW 875.14)
4) 1-Palmitoyl-2-lauroyl compound
sodium salt; $C_{37}H_{72}NaO_{12}P$ (MW 762.93)
5) 1-Stearoyl-2-lauroyl compound
sodium salt; $C_{39}H_{76}NaO_{12}P$ (MW 790.98)
6) 1-Stearoyl-2-myristoyl compound
sodium salt; $C_{41}H_{80}NaO_{12}P$ (MW 819.04)
7) 1-Stearoyl-2-palmitoyl compound
sodium salt; $C_{43}H_{84}NaO_{12}P$ (MW 847.09)

8. Examples of (sn)-1,2-diacyl-3-glycero-phospho-(sn)-1-glycero-glycol

1) Dipalmitoyl compound
sodium salt; C40 H80 Na O12 P (MW 789.04)
2) Distearoyl compound
sodium salt; C44 H86 Na O12 P (MW 845.14)
3) 1-Stearoyl-2-myristoyl compound
sodium salt; C40 H78 Na O12 P (MW 789.04)
4) 1-Stearoyl-2-palmitoyl compound
sodium salt; C42 H82 Na O12 P (MW 817.09)

9. Examples of (sn)-1,2-diacyl-3-glycero-phospho-(sn)-1-diglycero-glycol

1) Dipalmitoyl compound
sodium salt; C43 H84 Na O12 P (MW 863.12)
2) Distearoyl compound
sodium salt; C47 H90 Na O12 P (MW 919.22)

10. Examples of (sn)-1,2-diacyl-3-glycero-phospho-(sn)-1-triglycerol

1) Dipalmitoyl compound
sodium salt; C44 H86 Na O12 P (MW 893.12)
2) Distearoyl compound
sodium salt; C48 H92 Na O12 P (MW 949.22)

Item 1 Stimuli-sensitive nanocarrier system.
Item 2 Stimuli-sensitive nanocarrier system for use in locoregional therapy.
Item 3 Stimuli-sensitive nanocarrier system according to either item 1 or item 2,
characterised in that
said system is a thermosensitive liposome.

Item 4 Stimuli-sensitive nanocarrier system, in particular thermosensitive liposome, according to any of items 1 to 3,
characterised in that said system comprises
(i) at least one phosphatidylcholine having a main transition temperature of from 0° C. to 80° C. and
(ii) at least one phosphatidyloligoglycerol and/or at least one phosphatidylglyceroglycol and/or at least one cardiolipin.

Item 5 Stimuli-sensitive nanocarrier system, in particular thermosensitive liposome, according to any of items 1 to 4,
characterised in that
said system comprises at least one phosphatidyloligoglycerol of formula (II)

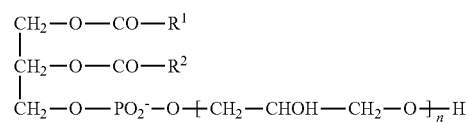

wherein $R^1$ and $R^2$ each independently represent a hydrocarbon functional group having from 12 to 24 carbon atoms and n is an integer from 2 to 50.

Item 6 Stimuli-sensitive nanocarrier system, in particular thermosensitive liposome, according to any of items 1 to 4,
characterised in that
said system comprises at least one phosphatidyloligoglycerol of formula (IIa)

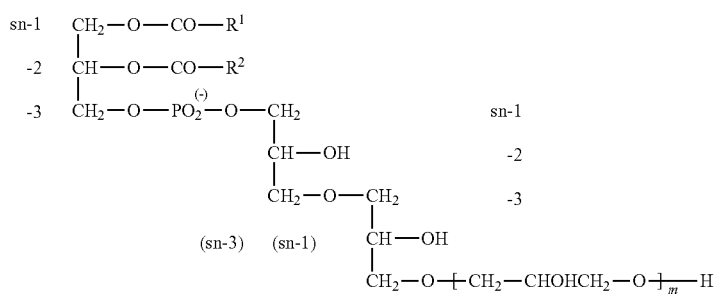

wherein $R^1$ and $R^2$ each independently represent a hydrocarbon functional group having from 12 to 24 carbon atoms and m is an integer from 0 to 50, wherein the linkage from the glyceride to the phosphate group is stereospecific and is in the form of an sn-3 linkage and the linkage from the phosphate group to the oligoglycerol is stereospecific and is in the form of an sn-1 linkage.

Item 7 Stimuli-sensitive nanocarrier system, in particular thermosensitive liposome, according to either item 5 or item 6,
characterised in that
$R^1$ and $R^2$ independently of one another are a linear saturated C12- to C24-alkyl functional group and n is 2 or 3 or m is 0 or 1.

Item 8 Stimuli-sensitive nanocarrier system, in particular thermosensitive liposome, according to any of items 4 to 7,
characterised in that
said system comprises at least one phosphatidyldiglycerol and/or at least one phosphatidyltriglycerol.

Item 9 Stimuli-sensitive nanocarrier system, in particular thermosensitive liposome, according to any of items 1 to 8, comprising a phosphatidylcholine of formula (I)

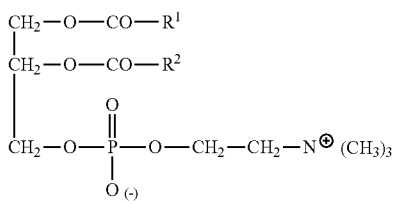

wherein $R^1$ and $R^2$ each independently represent a hydrocarbon functional group having from 12 to 24 carbon atoms.

Item 10 Stimuli-sensitive nanocarrier system, in particular thermosensitive liposome, according to any of the preceding items,
characterised in that
said system comprises at least one phosphatidylcholine selected from the group consisting of 1-palmitoyl-2-oleoylglycero-3-phosphocholine, 1-stearoyl-2-oleoyl-3-phosphocholine, 1-palmitoyl-2-lauroylglycero-3-phosphocholine, 1-behenoyl-2-oleoylglycero-3-phosphocholine, 1-stearoyl-2-lauroylglycero-3-phosphocholine, 1,3-dimyristoylglycero-2-phosphocholine, 1,2-dimyristoylglycero-3-phosphocholine, 1-palmitoyl-2-myristoylglycero-3-phosphocholine, 1-stearoyl-2-myristoylglycero-3-phosphocholine, 1-myristoyl-2-palmitoylglycero-3-phosphocholine, 1,3-palmitoylglycero-2-phosphocholine, 1,2-dipalmitoylglycero-3-phosphocholine, 1-myristoyl-2-stearoylglycero-3-phosphocholine, 1-stearoyl-3-myristoylglycero-2-phosphocholine, 1-stearoyl-2-palmitoylglycero-3-phosphocholine, 1-palmitoyl-2-stearoylglycero-3-phosphocholine, 1,3-distearoylglycero-2-phosphocholine, 1,2-distearoylglycero-3-phosphocholine, 1,2-diarachinoylglycero-3-phosphocholine, 1,2-dibehenoylglycero-3-phosphocholine and 1,2-dilignoceroylglycero-3-phosphocholine.

Item 11 Stimuli-sensitive nanocarrier system, in particular thermosensitive liposome, according to any of the preceding items,
characterised in that
said system comprises at least one phosphatidylcholine having a main transition temperature in the range of from 35° C. to 42° C. or in the range of from 40° C. to 43° C.

Item 12 Stimuli-sensitive nanocarrier system, in particular thermosensitive liposome, according to either item 10 or item 11,
characterised in that
said system comprises at least one phosphatidylcholine selected from 1,3-dipalmitoylphosphatidylcholine and 1,2-dipalmitoylphosphatidylcholine.

Item 13 Stimuli-sensitive nanocarrier system, in particular thermosensitive liposome, according to any of the preceding items,
characterised in that
it does not comprise cholesterol.

Item 14 Stimuli-sensitive nanocarrier system, in particular thermosensitive liposome, according to any of the preceding items for use in the treatment of tumours.

Item 15 Stimuli-sensitive nanocarrier system, in particular thermosensitive liposome, according to item 14 for use in the treatment of soft-tissue sarcoma, osteosarcoma, bladder carcinoma (muscle invasive bladder cancer [MIBC] and non-muscle invasive bladder cancer [NMIBC]), ovarian carcinoma, stomach carcinoma, breast carcinoma (especially triple negative breast cancer [TNBC]), hepatocellular carcinoma, uterine carcinoma, carcinoma of the thyroid gland, head-neck tumours, prostate carcinoma, chordoma, desmoid tumour, glioblastoma and other tumour diseases having preferably locoregional spread.

Item 16 Stimuli-sensitive nanocarrier system, in particular thermosensitive liposome, according to either item 14 or item 15 for use in the treatment of bladder tumours.

Item 17 Stimuli-sensitive nanocarrier system, in particular thermosensitive liposome, according to any of items 14 to 16, further comprising an active ingredient, in particular selected from anthracyclines (for example doxorubicin, epirubicin), oxazaphosphorines (for example hydroxyifosfamide), platinum analogues (cisplatin, oxaliplatin, carboplatin), gemcitabine, 5-fluorouracil, paclitaxel, docetaxel, etoposide, topotecan, vincristine, irinotecan, methotrexate, bleomycin, tyrosine kinase inhibitors, small molecules, DNA therapeutics, radiosensitisers (in conjunction with radiotherapy).

Item 18 Stimuli-sensitive nanocarrier system, in particular thermosensitive liposome, according to any of items 1 to 13 for use in the treatment of infectious diseases.

Item 19 Stimuli-sensitive nanocarrier system, in particular thermosensitive liposome, according to item 18,
characterised in that
the infectious disease is caused by bacteria, viruses, fungi and/or parasites.

Item 20 Stimuli-sensitive nanocarrier system, in particular thermosensitive liposome, according to either item 18 or item 19 for the treatment of infections of medical implants, in particular orthopaedic prostheses, for the treatment of localised infections, in particular infections of the deep soft tissue and/or of the bone, and/or for the therapy of multiresistant pathogens.

Item 21 Stimuli-sensitive nanocarrier system, in particular thermosensitive liposome, according to any of items 18 to 20, further comprising an active ingredient, in particular selected from antibiotics, virostatics, fungicides, and medicinal drugs having an anti-parasitic effect.

Item 22 Stimuli-sensitive nanocarrier system, in particular thermosensitive liposome, according to any of items 18 to 21,
characterised in that
the active ingredient is selected from
antibiotics, in particular β-lactams, glycopeptides, polyketides, aminoglycoside antibiotics, polypeptide antibiotics, quinolones, sulfonamides (for example linezolid, flucloxacillin, cefazolin, clindamycin, vancomycin, teicoplanin, rifampicin, ampicillin, ceftazidime, ceftriaxone, cefepime, piperacillin, fluoroquinolones, metronidazole, amikacin, etc.) and/or
virostatics, in particular entry inhibitors, penetration inhibitors, DNA polymerase inhibitors, DNA/RNA polymerase inhibitors, reverse transcriptase inhibitors, inosine monophosphate dehydrogenase inhibitors, protease inhibitors, integrase inhibitors, helicase-primase inhibitors, cyclophilin inhibitors, maturation inhibitors, terminase inhibitors, neuraminidase inhibitors, etc., and/or fungicides, in particular azoles (benzimidazoles ("MBC"), triazoles, imidazoles), morpholines, strobilurins, quinolines, anilino-pyrimidines, oxazolidine-diones, carboxylic acid amides, etc.

Item 23 Stimuli-sensitive nanocarrier system, in particular thermosensitive liposome, according to any of items 1 to 13 for use in the treatment of diseases of the eye.

Item 24 Stimuli-sensitive nanocarrier system, in particular thermosensitive liposome, according to item 23 for the treatment of inflammatory, degenerative, infectious and/or neoplastic diseases of the eye, wound healing disorders and/or glaucoma.

Item 25 Stimuli-sensitive nanocarrier system, in particular thermosensitive liposome, according to any of items 1 to 13 for use in the treatment of autoimmune diseases.

Item 26 Stimuli-sensitive nanocarrier system, in particular thermosensitive liposome, according to item 25 for use in the treatment of rheumatoid arthritis and/or chronic inflammatory intestinal diseases.

Item 27 Stimuli-sensitive nanocarrier system, in particular thermosensitive liposome, according to either item 25 or item 26, further comprising an active ingredient, in particular a steroid, TNF-α and/or immunosuppressants.

Item 28 Stimuli-sensitive nanocarrier system, in particular thermosensitive liposome, according to any of items 1 to 13 for use in diagnosis.

Item 29 Stimuli-sensitive nanocarrier system, in particular thermosensitive liposome, according to item 28 for non-invasive temperature measurement using MR contrast agents and MR imaging.

Item 30 Stimuli-sensitive nanocarrier system, in particular thermosensitive liposome, according to either item 28 or item 29, further comprising an active ingredient, in particular a CT or MRT contrast agent, preferably selected from iodine-containing contrast agents or gadolinium chelates.

Item 31 Stimuli-sensitive nanocarrier system, in particular thermosensitive liposome, according to any of items 1 to 13 for use in the treatment of degenerative diseases.

Item 32 Stimuli-sensitive nanocarrier system, in particular thermosensitive liposome, according to item 31 for the localised release of anti-inflammatory agents, analgesics and/or chondroprotectants.

Item 33 Stimuli-sensitive nanocarrier system, in particular thermosensitive liposome, according to any of items 1 to 13 for use in the treatment of dementia syndromes, Alzheimer's disease and/or focal neurological psychiatric diseases, in particular epilepsy.

Item 34 Stimuli-sensitive nanocarrier system, in particular thermosensitive liposome, according to any of items 1 to 13 for use in the treatment of atherosclerosis.

Item 35 Stimuli-sensitive nanocarrier system, in particular thermosensitive liposome, according to any of items 1 to 13 for use in the treatment of thromboses.

Item 36 Stimuli-sensitive nanocarrier system, in particular thermosensitive liposome, according to item 35, further comprising at least one active ingredient, in particular selected from fibrinolytics, preferably streptokinase, urokinase and/or alteplase.

Item 37 Stimuli-sensitive nanocarrier system according to any of the preceding items, wherein the stimuli-sensitive nanocarrier system is changed and in particular opened by the exertion of a stimulus in order to release from the nanocarrier system an active ingredient which may be contained therein.

Item 38 Stimuli-sensitive nanocarrier system according to item 37, wherein the stimulus is selected from radio frequency (for example radiative superficial and deep hyperthermia systems, bladder hyperthermia systems), ultrasound (for example highly focused ultrasound [high intensity focused ultrasound, HIFU], low intensity ultrasound [low intensity focused ultrasound, LIFU]), light, laser, conduction through heated liquid, other physical principles which either lead to locoregional heating and/or can destabilise membranes consisting of phospholipids.

Item 39 Stimuli-sensitive nanocarrier system, in particular thermosensitive liposome, according to any of the preceding items 14 to 16,
characterised in that
said system further comprises a cytostatic.

Item 40 Stimuli-sensitive nanocarrier system, in particular thermosensitive liposome, according to item 39,
characterised in that
the cytostatic is selected from the group consisting of mitomycin C, doxorubicin, epirubicin, gemcitabine, trabectedin, cisplatin, carboplatin and oxaliplatin.

Item 41 Stimuli-sensitive nanocarrier system, in particular thermosensitive liposome, according to any of the preceding items in combination with hyperthermia and/or ultrasound.

Item 42 Stereospecific phosphatidyloligoglycerol of formula (IIa)

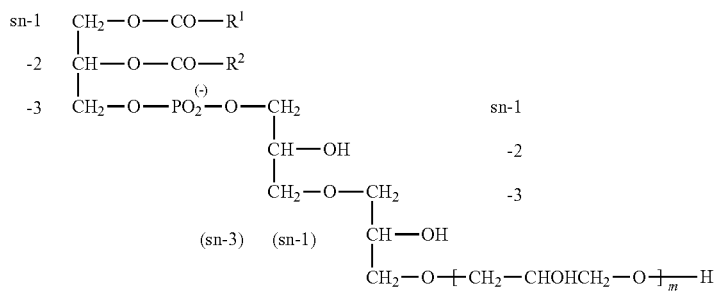

Configuration: natural
Name: 1,2-diacyl-sn-3-glycero-phospho-sn-1-oligoglycerol;
sn, stereospecific numbering;
wherein $R^1$ and $R^2$ each independently represent a hydrocarbon functional group having from 12 to 24 carbon atoms and m is an integer from 0 to 50, wherein the linkage from the glyceride to the phosphate group is stereospecific and is in the form of an sn-3 linkage and the linkage from the phosphate group to the oligoglycerol is stereospecific and is in the form of an sn-1 linkage.

Item 43 Stimuli-sensitive liposome comprising a stereospecific phosphatidyloligoglycerol of formula (IIa) according to item 42 for use in the treatment of bladder tumours.

Item 44 Stimuli-sensitive liposome according to item 43, further comprising a phosphatidylcholine of formula (I) having a main transition temperature of from 35 to 40° C., in particular from 40 to 43° C.

The invention claimed is:

1. A stimuli-sensitive nanocarrier system comprising at least one phosphatidyloligoglycerol of formula (IIa)

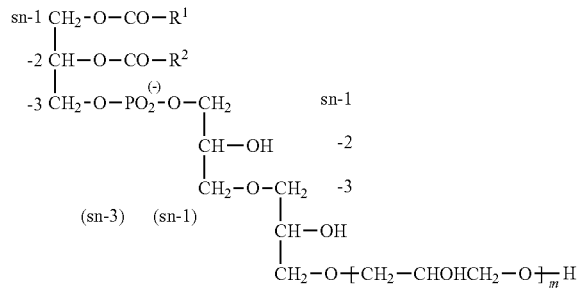

wherein $R^1$ and $R^2$ each independently represent a hydrocarbon functional group having from 12 to 24 carbon atoms and m is an integer from 0 to 50, wherein the linkage from the glyceride to the phosphate group is stereospecific and is in the form of an sn-3 linkage and the linkage from the phosphate group to the oligoglycerol is stereospecific and is in the form of an sn-1 linkage.

2. The stimuli-sensitive nanocarrier system of claim 1, wherein the system is a thermosensitive liposome.

3. The stimuli-sensitive nanocarrier system of claim 1, the system comprising:
(i) at least one phosphatidylcholine having a main transition temperature of from 0° C. to 80° C.; and,
(ii) at least one phosphatidyloligoglycerol and/or at least one phosphatidylglyceroglycol and/or at least one cardiolipin.

4. The stimuli-sensitive nanocarrier system of claim 1, wherein $R^1$ and $R^2$ independently of one another are a linear saturated C12- to C24-alkyl functional group and m is 0 or 1.

5. The stimuli-sensitive nanocarrier system of claim 1, the system further comprising at least one phosphatidyldiglycerol and/or at least one phosphatidyltriglycerol.

6. The stimuli-sensitive nanocarrier system of claim 1 further comprising a phosphatidylcholine of formula (I)

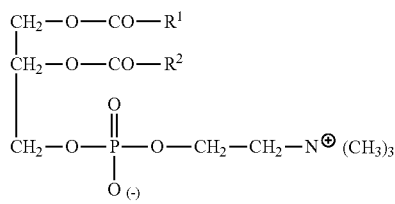

wherein $R^1$ and $R^2$ each independently represent a hydrocarbon functional group having from 12 to 24 carbon atoms.

7. The stimuli-sensitive nanocarrier system of claim 1 comprising at least one phosphatidylcholine selected from the group consisting of 1-palmitoyl-2-oleoylglycero-3-phosphocholine, 1-stearoyl-2-oleoyl-3-phosphocholine, 1-palmitoyl-2-lauroylglycero-3-phosphocholine, 1-behenoyl-2-oleoylglycero-3-phosphocholine, 1-stearoyl-2-lauroylglycero-3-phosphocholine, 1,3-dimyristoylglycero-2-phosphocholine, 1,2-dimyristoylglycero-3-phosphocholine, 1-palmitoyl-2-myristoylglycero-3-phosphocholine, 1-stearoyl-2-myristoyl-glycero-3-phosphocholine, 1-myristoyl-2-palmitoylglycero-3-phosphocholine, 1,3-palmitoylglycero-2-phosphocholine, 1,2-dipalmitoylglycero-3-phosphocholine, 1-myristoyl-2 stearoylglycero-3-phosphocholine, 1-stearoyl-3 myristoyl-glycero-2-phosphocholine, 1-stearoyl-2-palmitoylglycero-3-phosphocholine, 1 palmitoyl-2-stearoylglycero-3-phosphocholine, 1,3-di stearoylglycero-2-phosphocholine, 1,2-distearoylglycero-3-phosphocholine, 1,2-diarachinoylglycero-3-phosphocholine, 1,2-dibehenoylglycero-3-phosphocholine and 1,2-dilignoceroylglycero-3-phosphocholine.

8. The stimuli-sensitive nanocarrier system of claim 1 comprising at least one phosphatidylcholine having a main transition temperature in the range of from 35° C. to 42° C. or in the range of from 40° C. to 43° C.

9. The stimuli-sensitive nanocarrier system of claim 8, wherein the at least one phosphatidylcholine is 1,3-dipalmitoyl-phosphatidylcholine or 1,2-dipalmitoylphosphatidylcholine.

10. The stimuli-sensitive nanocarrier system of claim 1, wherein the system does not comprise cholesterol.

11. A method for treating a tumor in an individual having the tumor comprising administration of the stimuli-sensitive nanocarrier system of claim 1 to the individual.

12. The method of claim 11 wherein the tumor is a soft-tissue sarcoma, osteosarcoma, bladder carcinoma, ovarian carcinoma, stomach carcinoma, breast carcinoma, hepatocellular carcinoma, uterine carcinoma, carcinoma of the thyroid gland, head-neck tumor, prostate carcinoma, chordoma, desmoid tumour, glioblastoma or other tumor disease.

13. The method of claim 11 wherein the tumor is a bladder tumor.

14. The method of claim 11 wherein the stimuli-sensitive nanocarrier system further comprises an active ingredient selected from the group consisting of anthracyclines, oxazaphosphorines, platinum analogues, gemcitabine, 5-fluorouracil, paclitaxel, docetaxel, etoposide, topotecan, vincristine, irinotecan, methotrexate, bleomycin, tyrosine kinase inhibitors, small molecules, DNA therapeutics and radiosensitisers.

15. The method of claim 11 wherein the stimuli-sensitive nanocarrier system further comprises a cytostatic selected from the group consisting of mitomycin C, doxorubicin, epirubicin, gemcitabine, trabectedin, cisplatin, carboplatin and oxaliplatin.

16. A method for treating infectious disease in an individual having the infectious disease comprising administration of the stimuli-sensitive nanocarrier system of claim 1 to the individual.

17. The method of claim 16 wherein the infectious disease is caused by bacteria, viruses, fungi and/or parasites.

18. The method of claim 16 wherein the infectious disease is an infection of a medical implant, a localized infection and/or an infection caused by multiresistant pathogens.

19. The method of claim 16, the stimuli-sensitive nanocarrier system further comprising an active ingredient selected from the group consisting of antibiotics, virostatics, fungicides and medicinal drugs having an anti-parasitic effect.

20. The method of claim 16, the stimuli-sensitive nanocarrier system further comprising an active ingredient selected from the group consisting of antibiotics, virostatics and fungicides.

21. A method for treating an individual having an eye disease comprising administration of the stimuli-sensitive nanocarrier system of claim 1 to the individual.

22. The method of claim 21, wherein the eye disease is an inflammatory disease, a degenerative disease, an infectious disease and/or a neoplastic disease, a wound healing disorder and/or glaucoma.

23. A method for treating an individual having an autoimmune disease comprising administration of the stimuli-sensitive nanocarrier system of claim 1 to the individual.

24. The method of claim 23, wherein the autoimmune disease is rheumatoid arthritis and/or a chronic inflammatory intestinal disease.

25. The method of claim 23, wherein the stimuli-sensitive nanocarrier system further comprises an active ingredient.

26. The method of claim 25, wherein the active ingredient is a steroid, TNF-α and/or an immunosuppressant.

27. A method for performing a diagnosis comprising using the stimuli-sensitive nanocarrier system of claim 1.

28. The method of claim 27, further comprising using an MR contrast agent and MR imaging.

29. The method of claim 27, further comprising using an active ingredient.

30. The method of claim 29, wherein the active ingredient is a CT or MRT contrast agent.

31. A method for treating an individual having a degenerative disease comprising administration of the stimuli-sensitive nanocarrier system of claim 1 to the individual.

32. The method of claim 31, wherein the stimuli-sensitive nanocarrier system further comprises an active ingredient selected from the group consisting of anti-inflammatory agents, analgesics and/or chondroprotectants.

33. A method for treating an individual having dementia, Alzheimer's disease and/or a focal neurological psychiatric disease comprising administration of the stimuli-sensitive nanocarrier system of claim 1 to the individual.

34. A method for treating an individual having atherosclerosis comprising administration of the stimuli-sensitive nanocarrier system of claim 1 to the individual.

35. A method for treating an individual having a thrombosis comprising administration of the stimuli-sensitive nanocarrier system of claim 1 to the individual.

36. The method of claim 35, wherein the stimuli-sensitive nanocarrier system further comprises an active ingredient comprising a fibrinolytic.

37. The stimuli-sensitive nanocarrier system of claim 1, wherein the stimuli is hyperthermia and/or ultrasound.

38. A stereospecific phosphatidyloligoglycerol of formula (IIa)

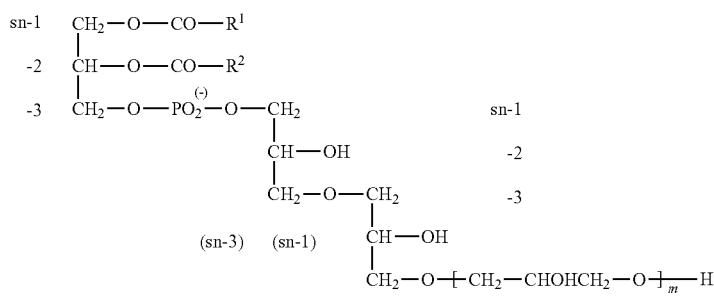

wherein $R^1$ and $R^2$ each independently represent a hydrocarbon functional group having from 12 to 24 carbon atoms and m is an integer from 0 to 50, wherein the linkage from the glyceride to the phosphate group is stereospecific and is in the form of an sn-3 linkage and the linkage from the phosphate group to the oligoglycerol is stereospecific and is in the form of an sn-1 linkage.

* * * * *

UNITED STATES PATENT AND TRADEMARK OFFICE
CERTIFICATE OF CORRECTION

PATENT NO.        : 10,251,838 B2
APPLICATION NO.   : 14/899174
DATED             : April 9, 2019
INVENTOR(S)       : Hansjörg Eibl Page 1 of 5

It is certified that error appears in the above-identified patent and that said Letters Patent is hereby corrected as shown below:

In the Specification

Column 5, Lines 15-24, please delete " 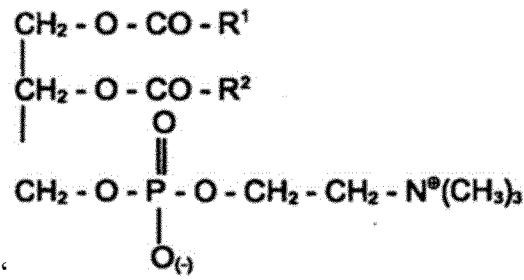 " and replace with

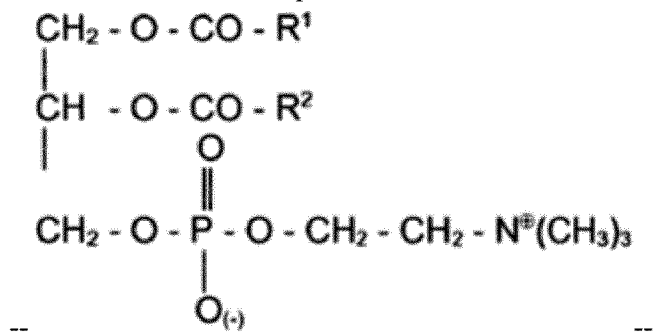

Column 6, Line 44, please delete "CaO" and replace with -- can --

Column 6, Lines 57-64, please delete " 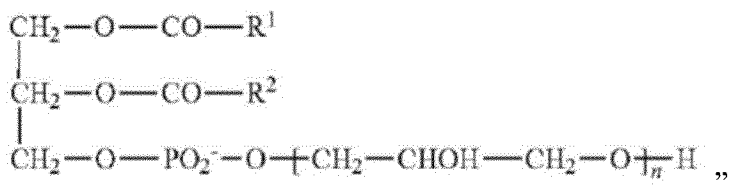 "

Signed and Sealed this
Eleventh Day of February, 2020

Andrei Iancu
*Director of the United States Patent and Trademark Office* and replace with 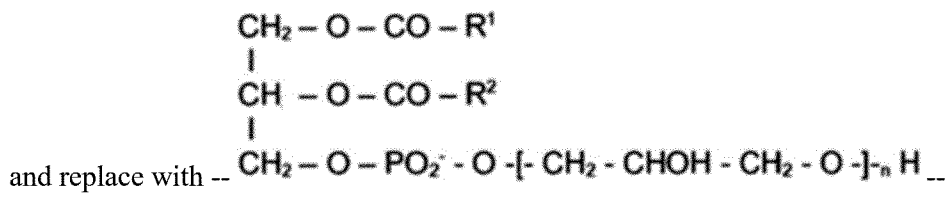
Column 7, Lines 44-55, please delete 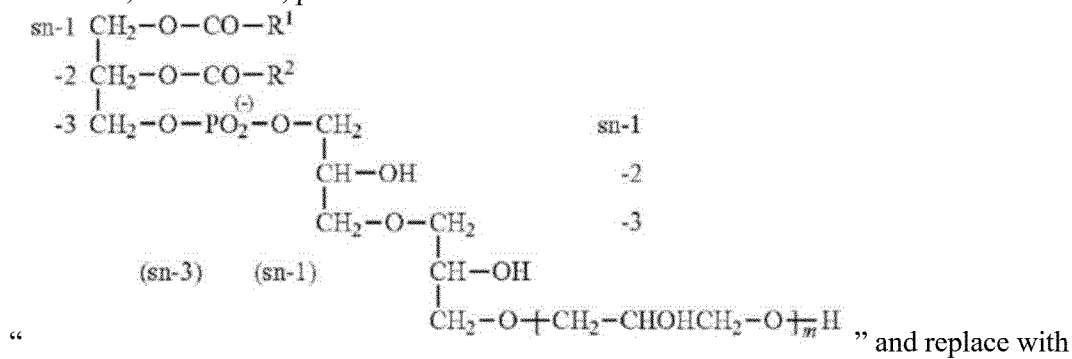 " and replace with 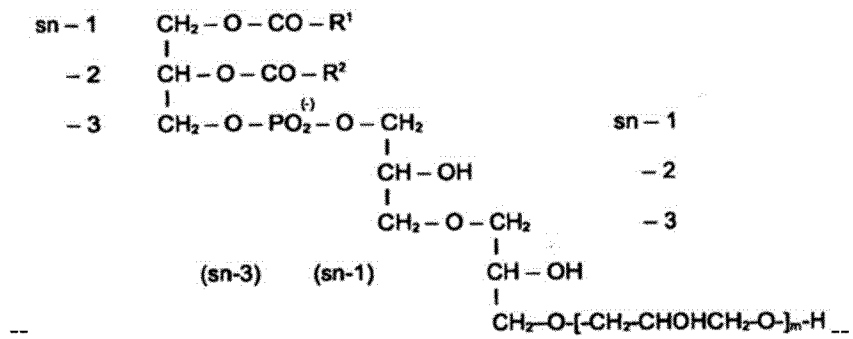 --
Column 16, Line 57, please delete "??"
Column 18, Line 63, please delete "tri-OF tetra-glycerols" and replace with -- tri- or tetra-glycerols --

CERTIFICATE OF CORRECTION (continued)
U.S. Pat. No. 10,251,838 B2

Column 20, Lines 31-46, please delete " 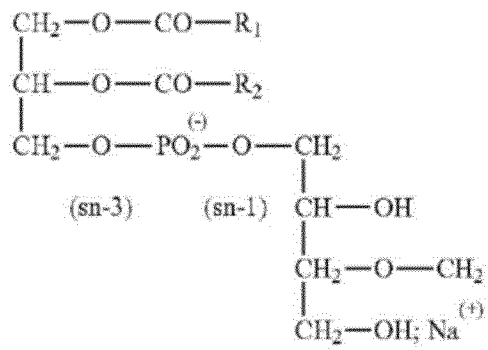 " and replace with -

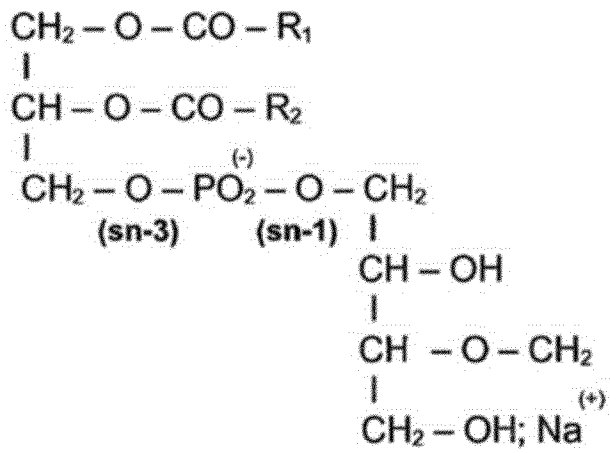

1) 1P-2P-sn-G-3-PO$_4$-(sn-1)-G-Gly; Na$^{(+)}$ 2) 1S-2S-sn-G-3-PO$_4$-(sn-1)-G-Gly; Na$^{(+)}$ --

Column 26, Line 48, please delete "P$_3$_third" and replace with -- P$_3$-third --

CERTIFICATE OF CORRECTION (continued)
U.S. Pat. No. 10,251,838 B2

Columns 27-28, please delete " 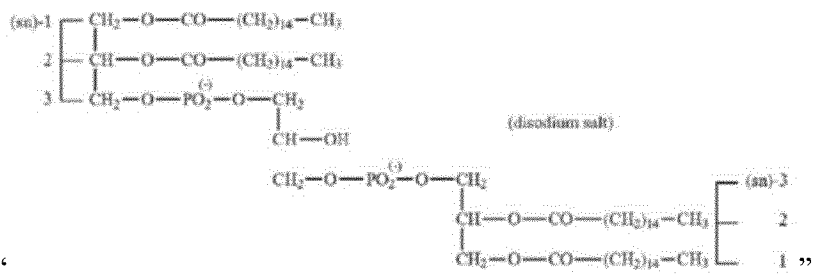

and replace with -- 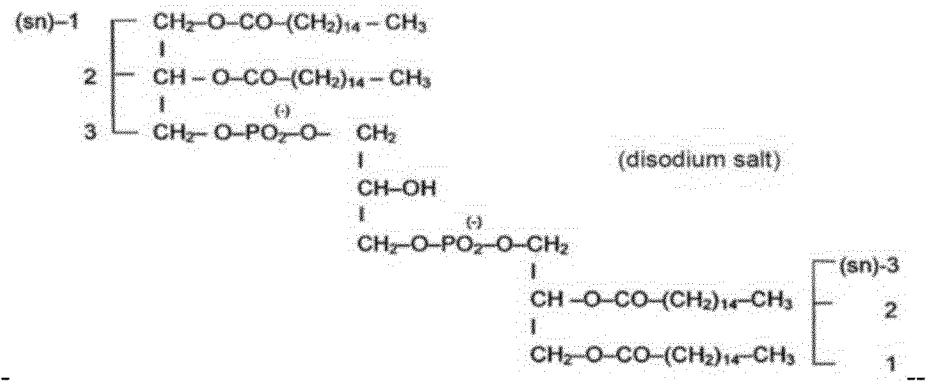 --

Column 30, Lines 6-7, please delete "transi ion" and replace with -- transition --

Column 30, Lines 20-25, please delete " 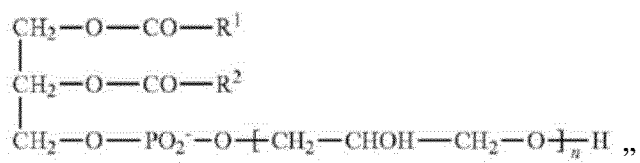 "

and replace with -- 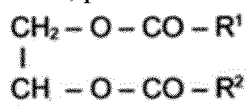 --

Column 31, Lines 10-20, please delete " 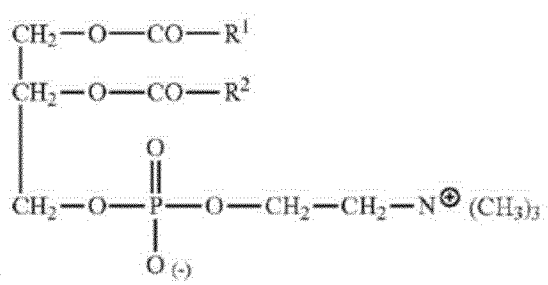 "

CERTIFICATE OF CORRECTION (continued)
U.S. Pat. No. 10,251,838 B2 and replace with -- 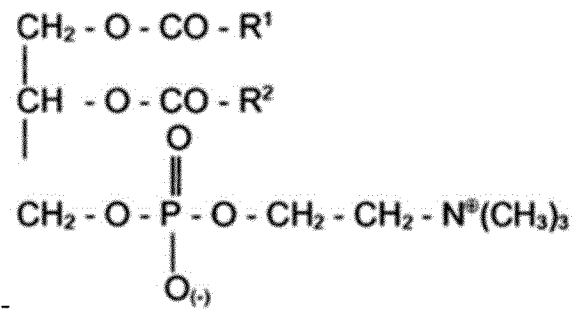 --

In the Claims

Column 35, In Claim 6, Lines 57-66, please delete " 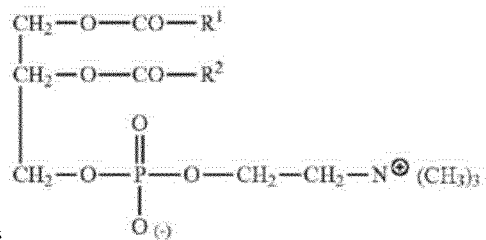 " and replace with -- 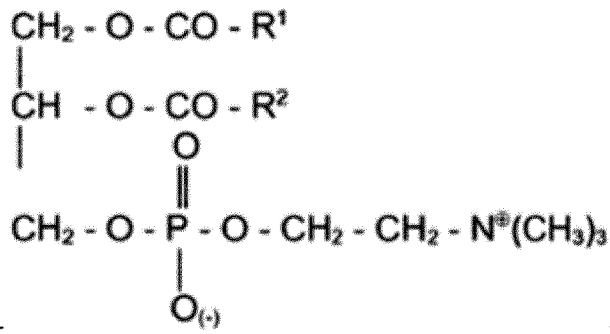 --